United States Patent [19]

Kennedy et al.

[11] Patent Number: 5,424,471
[45] Date of Patent: Jun. 13, 1995

[54] CRYSTALLINE AMIFOSTINE COMPOSITIONS AND METHODS OF THE PREPARATION AND USE OF SAME

[75] Inventors: Paul E. Kennedy, Phoenixville, Pa.; Roger A. Rajewski, Lawrence, Kans.; John M. Baldoni, Glenmore, Pa.

[73] Assignee: U.S. Bioscience, Inc., West Conshohocken, Pa.

[21] Appl. No.: 99,298

[22] Filed: Jul. 29, 1993

Related U.S. Application Data

[63] Continuation-in-part of Ser. No. 922,929, Jul. 31, 1992, abandoned.

[51] Int. Cl.$^6$ .............................................. C07F 9/165
[52] U.S. Cl. ..................................... 558/146; 558/166
[58] Field of Search ................................ 558/146, 166

[56] References Cited

U.S. PATENT DOCUMENTS 3,892,824  7/1975  Piper et al. ......................... 558/166
4,424,216  1/1984  Cerami et al. ...................... 514/114

FOREIGN PATENT DOCUMENTS 5404672  4/1979  Japan .

OTHER PUBLICATIONS

Eichler et al. "Radiation Inactivation Analysis of Enzymes" J. Biol. Chem. 1984, 262(20) 9433–9436.
Starke and Farber, "Ferric Iron and Superoxide Ions are Required for the Killing of Cultured Hepatocytes by Hydrogen Peroxide", J. Biol. Chem. 1985, 260(18), 10099.
Geary et al., "Characterization of Ethiofos Absorption in the Rat Small Intestine", Biopharmaceutics & Drug Disposition 1991, 12, 261–274.
Geary et al., "Characterization of WR–1065 Absorption in the Rat Small Intestine", Biopharmaceutics & Drug Disposition 1991, 12 75–284.
Zadeii et al., "Stability of Ethiofos (NSC-29691) in Aqueous Solution and Solid Phase Formulation", Pharm. Res. (NY) 1991, 8(10 Suppl.):S172.
Treskes et al., "Time Dependence of the Selective Modulation of Cisplaxin-induced Nephrotoxicity by WR 2721 in the Mouse", Cancer Res. 1992, 52, 2257–2260.
Karle JM et al. "Structure of the Radiation Protection Agent S-2(3-Aminopropylamino)ethylphosphorothioic Acid (WR 2721)." Acta Cryst. (1988). C44, 135–138.

*Primary Examiner*—Mary C. Lee
*Assistant Examiner*—Michael G. Ambrose
*Attorney, Agent, or Firm*—Pennie & Edmonds

[57] ABSTRACT

The present invention relates to a sterile, stable vacuum dried crystalline amifostine composition and, optionally, pharmaceutically acceptable excipient(s). Typically, the crystalline compositions of the present invention exhibit enhanced stability at temperatures ranging from about 4° C. to about ambient temperature for a period of at least 2 years relative to existing solid vacuum dried amorphous amifostine preparations. The reconstituted compositions of the present invention are suitable for administration to humans as a radio- or chemoprotecting agent.

33 Claims, 13 Drawing Sheets

■ 25°C   □ 10°C   ○ 5°C
◇ 0°C    ● -5°C   ▲ -10°C

WR-2721 Drug Substance

CRYSTALLINE AMIFOSTINE COMPOSITIONS AND METHODS OF THE PREPARATION AND USE OF SAME

This application is a continuation-in-part of U.S. application Ser. No. 07/922,929, filed Jul. 31, 1992, now abandoned.

FIELD OF THE INVENTION

The present invention relates to sterile, particulate-free crystalline S-2-(3-aminopropylamino) ethyl dihydrogen phosphorothioate (amifostine) formulations which provide improved stability.

BACKGROUND OF THE INVENTION

The compound S-2-(3-aminopropylamino)ethyl dihydrogen phosphorothioate (which is also known as amifostine, ethiofos, Ethyol®, NSC 296961, and WR-2721 and which will hereinafter be referred to as "amifostine") and other aminoalkyl dihydrogen phosphorothioates are disclosed in U.S. Pat. No. 3,892,824 to Piper et al. This patent also discloses the known process for making a crystalline form of amifostine drug substance and is incorporated herein by reference. This crystalline form of amifostine has been shown to be relatively stable at room temperature for several years as well as at 50° C. for several months. These compounds were originally developed as antiradiation agents (radioprotectants), in particular to be used against x-ray or nuclear radiation which may be encountered during military conflicts.

In addition to its utility as a military antiradiation agent, amifostine has demonstrated excellent utility as a non-military radioprotectant and chemoprotectant i.e., as a protectant for the undesirable adverse effects which arise during the use of radiation therapy in the treatment of cancer and the use of chemotherapeutic agents, for example, alkylating agents such as cyclophosphamide, cisplatin, carboplatin, doxorubicin and its derivatives, and mitomycin and its derivatives. Similarly, it has been reported that amifostine has been used experimentally to protect HIV infected patients (AIDS) from the harmful side effects of 3'-azido-3'-deoxythymidine (AZT) therapy. Amifostine and its derivatives exert their protective effects without significantly affecting the beneficial properties of the administered therapeutic agents. This is in part due to the selective uptake of the protective thiol into normal tissue.

As used herein, the term "amifostine drug substance" refers to its pre-vacuum dried or pre-vacuum dried state which is available on an "as is" basis in a trihydrate form. Currently available sterile, vacuum dried formulations of amifostine drug product will be referred to as "amorphous amifostine", whereas the form covered by the present invention will be referred to as "crystalline amifostine" in order to distinguish between the two forms. Unless otherwise specified, quantities reported herein shall be calculated on an anhydrous basis.

Although amifostine has many advantageous properties, extensive difficulty has been encountered in trying to obtain a convenient, stable, sterile dosage formulation.

The present manner of manufacturing and packaging amifostine comprises the steps of filling into pre-sterilized vials a sterilized water solution comprising amifostine to a predetermined volume, cooling the vials and their contents, and removing the solvent by lyophilization to produce dried amifostine of a predetermined amount in each vial. [See L. Lachman, et al. The Theory and Practice of Industrial Pharmacy p 62–63, 1986]. This avoids substantial practical problems related to the packaging of bulk, solid amifostine using the so-called "dry filling" or "powder filling" method. Such problems include the difficulty in the manual manipulation of powders, the need to mill the powders to acceptable particle size and flowability, difficulty in maintaining particle-free, aseptic conditions, and the difficulty in supplying the precise dosage of solid amifostine into each vial.

However, the currently available formulation of amifostine. This amorphous form that is produced by lyophilization is thermally unstable. As a result, this lyophilized formulation must be maintained at temperatures at about −20° C. and shipped at temperatures at about −70° C. to about −20° C. to avoid degradation of the formulated product. The need for low temperature during shipping and storage is an obstacle and shortcoming of currently available vacuum dried forms of amifostine. Special packaging and significant expenses are involved in the shipping and storage of the product. Moreover, hospitals without freezer storage conditions will be unable to supply amifostine for use to their patients (e.g., third world markets would be extensively hindered from using amifostine). However, since no alternative formulations were available, clinical trials were conducted using this formulation.

Hence, there is a need to develop a dosage form which has sufficient stability to provide a long shelf life at room temperature or under less stringent refrigeration, which is not uncommon for many drug products.

The present invention describes new and novel procedures which produce solid compositions containing vacuum dried amifostine, with and without pharmaceutically acceptable excipients such as mannitol, which have improved stability over the previously available composition.

SUMMARY OF THE INVENTION

The present invention relates to a process for the preparation of crystalline compositions comprising the steps of (a) preparing a formulation comprising an aminoalkyl dihydrogen phosphorothioate of the formula $RHN(CH_2)_nNH(CH_2)_mSPO_3H_2$ or its hydrates or alkali metal salts, in which R is H or $C_1$-$C_7$ alkyl, and n and m may be independently an integer from 2–6, an alcohol and water solvent solution in which the relative amounts of aminoalkyl dihydrogen phosphorothioate, alcohol and water are such that a particulate-free solution is obtained at temperatures ranging from about room temperature to about 10° C., but which provides a crystalline precipitate of aminoalkyl dihydrogen phosphorothioate upon cooling below 0° C.; (b) cooling the formulation to a temperature below 0° C. for a period of time sufficient to effect the precipitation of the crystalline aminoalkyl dihydrogen phosphorothioate; and (c) vacuum drying the resulting mixture to leave a solid crystalline preparation having an enhanced temperature stability. As a further step in the present invention, a sterile inert gas such as argon, nitrogen and helium can be introduced over the preparation. Preferably, the temperature to which the formulation is cooled to initiate precipitation of the crystalline aminoalkyl dihydrogen phosphorothioate is in the range of the eutectic point of the formulation. Optimally, the formulation may also contain excipients such as mannitol.

Aminoalkyl dihydrogen phosphorothioates suitable for use in the present invention include, but are not limited to, S-2-(3-aminopropylamino)ethyl dihydrogen phosphorothioate (amifostine), S-2-(3-methylaminopropylamino)ethyl dihydrogen phosphorothioate (WR-3689), S-2-(3-ethylaminopropylamino)ethyl dihydrogen phosphorothioate, S-2-(3-aminopropylamino)-2-methylpropyl dihydrogen phosphorothioate, S-2-(2-aminoethylamino)-2-ethyl dihydrogen phosphorothioate, S-2-(4-aminobutylamino)-2-ethyl dihydrogen phosphorothioate, S-2-(5-aminopentylamino)-2-ethyl dihydrogen phosphorothioate, S-2-(6-aminohexylamino)-2-ethyl dihydrogen phosphorothioate, S-2-(2-methylaminoethylamino)-2-ethyl dihydrogen phosphorothioate, S-2-(3-methylaminopropylamino)-2-ethyl dihydrogen phosphorothioate, and S-3-(3-methylaminopropylamino)-3-propyl dihydrogen phosphorothioate (WR-151327). In a preferred embodiment, the aminoalkyl dihydrogen phosphorothioate is amifostine, WR-3689, WR-151327, most preferably amifostine. Alcohols suitable to effect crystalline precipitation of aminoalkyl dihydrogen phosphorothioate for use in the present process include, but are not limited to, $C_1$-$C_5$ alkyl alcohols, such as methanol, ethanol, propanol, isopropanol, n-butanol, sec-butanol, tert-butanol, n-pentanol, 2-pentanol, and the like, preferably ethanol.

In a particular process of the invention, the temperature of the mixture resulting from step (b) is raised to an annealing temperature that lies about 1° to about 20° C. above the eutectic temperature of the formulation, followed by cooling the temperature of the mixture from the annealing temperature back to the eutectic temperature or below prior to performing the vacuum drying of step (c). In specific instances, the eutectic temperature may fall in the range of about −80° C. to about 0° C., while the annealing temperature may fall in the range of about −30° C. to about 10° C.

Thus, it is an objective of the present invention to provide a process in which the formulation comprises about 50 to about 400 mg aminoalkyl dihydrogen phosphorothioate per ml of formulation, about 1–35% (v/v) alcohol, and about 65–99% (v/v) water. Preferably, the formulation comprises about 125 to about 250 mg aminoalkyl dihydrogen phosphorothioate per ml of formulation, about 5–20% (v/v) alcohol, and about 80–95% (v/v) water. Most preferably, the formulation comprises about 100 mg aminoalkyl dihydrogen phosphorothioate per ml of formulation, about 10% (v/v) alcohol, and about 90% (v/v) water.

The temperatures of the various cooling and vacuum drying steps can vary widely depending on the specific ratios of aminoalkyl dihydrogen phosphorothioate to alcohol to water. Generally, however, the temperatures of steps (b) and (c) fall in the range of about −40° C. to about −5° C., preferably about −20° C.

In a specific embodiment of the present invention, the process includes a sterilization step. Sterilization may be effected in any number of ways well know to those skilled in the art, such as heating the mixture in an autoclave, treatment with gamma radiation, aseptic recrystallization, or sterile filtering a solution, e.g., through a 0.2 μm pore size filter. It should be noted further that the crystalline aminoalkyl dihydrogen phosphorothioate may be anhydrous or contain solvents of crystallization. In particular, crystalline amifostine may be anhydrous, a solvate, or a hydrate, such as a monohydrate or a trihydrate. Generally, the hydrates may contain about 1 to about 5, preferably about 1 to about 3, moles of water of crystallization.

In an alternative procedure for preparing the formulation, the aminoalkyl dihydrogen phosphorothioate, such as amifostine, and any desired excipients are dissolved in Water for Injection, USP, and the resulting solution is then sterile filtered. Thereafter, the required amount of sterile alcohol such as sterile ethanol, USP is added to yield the formulation that is subsequently subjected to the cooling or annealing steps.

The formulation produced according to the disclosed process may further be comprised of a pharmaceutically acceptable excipient. Suitable excipients include, but are not limited to, sodium chloride, propylene glycol, sucrose, dextrose, sorbitol, inositol, mannitol, glycine, arginine, or other amino acids, preferably mannitol, and most preferably mannitol, NF.

Thus, it is a particular objective of the present invention to provide a process for the preparation of a pharmaceutical composition containing crystalline amifostine comprising the steps of (a) preparing a formulation comprising about 50 to about 300 mg amifostine per ml of the formulation, about 3 to about 30% (v/v) ethanol, about 70-97% (v/v) water, and, optionally, about 5 to about 300 mg of a pharmaceutically acceptable excipient per ml of the formulation, such that a particulate-free solution is obtained at temperatures ranging from about room temperature to about 10° C., but which provides a crystalline precipitate of amifostine upon cooling below 0° C.; (b) cooling the formulation to a temperature falling in the range of about −40° C. to about −5° C. for a period of time sufficient to effect the precipitation of the crystalline amifostine; and (c) vacuum drying the resulting mixture to leave a solid crystalline amifostine preparation having an enhanced temperature stability. In general, the steps taken after step (a) and before step (c) are carried out over a period of about 0.5 to about 72 hours, preferably about 2 to about 24 hours. Those manipulations taken at step (c) are carried out over a period of about 1 to about 72 hours, preferably about 10 to about 20 hours. In addition, the vacuum drying of step (c) is carried out at a vacuum of about 10 to about 1000 mTorr, preferably 150 mTorr.

Yet another object of the present invention concerns the preparation of a sterile pharmaceutical composition having an enhanced temperature stability in which the active ingredient, i.e., the crystalline aminoalkyl dihydrogen phosphorothioate, such as amifostine, remains stable at about 4° C. for at least 2 years. Preferably, the crystalline aminoalkyl dihydrogen phosphorothioate, such as amifostine, remains stable at about ambient temperature for at least 2 years. Thus, a sterile composition having an enhanced temperature stability is provided, which composition comprises a crystalline amifostine which can be reconstituted with a pharmaceutically acceptable vehicle into an injectable particulate-free drug product. Preferably, the sterile composition is provided as a sterile single dose formulation having an enhanced temperature stability comprising about 10 to about 10,000 mg crystalline amifostine and, optionally, about 10 to about 10,000 mg of a pharmaceutically acceptable excipient, which formulation can be reconstituted with a pharmaceutically acceptable vehicle into an injectable particulate-free drug product. In a more preferred embodiment, the sterile single dose formulation comprises about 100 to about 1000 mg crystalline amifostine and about 100 to about 1000 mg of an excipient. Most preferably, the sterile single dosage formulation comprises about 500 mg crystalline amifostine and about 500 mg mannitol. The vehicle may be chosen from a wide variety of pharmaceutically acceptable vehicles and may include Water for Injection, USP, Normal Saline, USP, 5% Dextrose in Water, USP, or aqueous buffers.

A further object of the present invention includes a method of treating a subject in need of radio- or chemoprotection, which comprises administering to the subject an effective amount of a pharmaceutical composition containing a crystalline aminoalkyl dihydrogen phosphorothioate having the generic chemical formula described above, such as amifostine, which has been reconstituted with a pharmaceutically acceptable vehicle. The reconstituted pharmaceutical composition may be administered parenterally. If desired, the reconstituted pharmaceutical composition may be administered intravenously, intramuscularly, subcutaneously, intracavetarily, and intrathecally.

These and other objects of the invention should be apparent to one of ordinary skill in the art from a reading of the general and detailed descriptions provided herein.

DETAILED DESCRIPTION OF THE INVENTION

Figure 1:
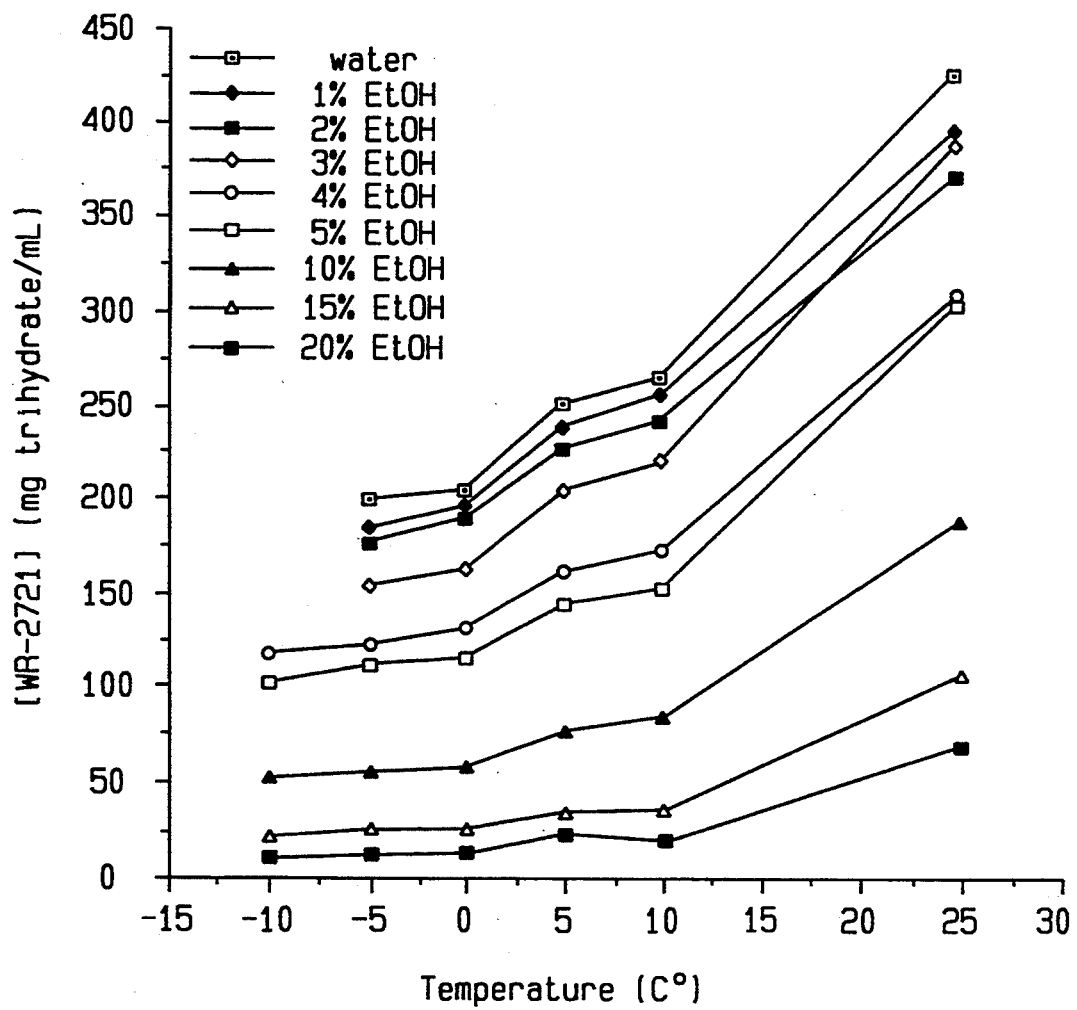
FIG. 1 Graph of Amifostine Drug Substance (WR-2721) Solubility in Aqueous/Ethanol Solutions vs. Temperature (° C.)

Prior to the present invention, the available pharmaceutical formulation of amifostine (Ethyol ®) was thermally unstable. Because of its instability, the Ethyol ® formulation required the use of low temperatures during shipping and storage in order to prevent product degradation.

The present invention provides the first stable, vacuum dried pharmaceutical formulation of amifostine which can be conveniently handled and stored at temperatures from about 4° C. to about room temperature for long periods of time without significant product degradation, thus providing a solution to a long sought need. The formulation will allow amifostine drug product to be shipped to and stored in hospitals around the world which do not have freezer storage capabilities required for the currently available formulation.

Unexpectedly, it has been discovered that a sterile and stable product of crystalline amifostine with and without excipient(s) such as mannitol can be prepared from the vacuum drying of an amifostine drug substance-containing hydro-ethanolic solution of about 1 to about 35% ethanol.

An important aspect of the present invention involved preformulation studies that determined (1) the solubility of amifostine drug substance (mg/ml) at various concentrations of water/ethanol, (2) the solubility of amifostine drug substance in water/ethanol at various temperatures, (3) the appropriate shelf temperature of the freeze-dryer needed to effect precipitation of amifostine before vacuum drying and (4) the concentration of ethanol needed in the formulation to give a super-saturated solution that when cooled to the desired shelf temperature in the freeze-dryer results in the precipitation of amifostine in a crystalline form. From the above preformulation studies (see Examples, infra) it was determined that the preferred concentration of amifostine, on an anhydrous basis, was about 100 mg/ml in about 10% aqueous ethanol. Further, a preferred shelf temperature of about −20° C. would effect precipitation of amifostine.

In order to obtain an elegant cake product, the percentage of ethanol in the ethanol/water mixture ranges from about 1 to about 35% v/v of ethanol (e.g., ratio of ethanol:water 1:99; 35:65); similarly, the shelf temperature of the freeze-dryer can range from about −40° C. to about −10° C., preferably −20° C. The results of the preformulation studies presented in this invention provide an important basis for adjustment of the interdependent variables of amifostine concentration, ethanol concentration and temperature to provide for multiple container size/fill volume combinations.

Generally, the freeze-dryer shelf is pre-chilled to a temperature of about −30° C. to about −15° C., preferably about −20° C. The vials are loaded and the temperature is readjusted to about −30° C. to about −15° C. and preferably −20° C. and the vials are maintained at this temperature for about 20 hours. Depending on the concentration of ethanol and amifostine or amifostine and excipient in the solutions, and depending on ethanol concentration, the temperature necessary to effect precipitation will vary accordingly. Next, the precipitation of crystalline amifostine takes place, followed by the freezing of the formulation.

Once the frozen formulation is observed, the primary drying cycle is initiated to remove bulk water and ethanol. Generally, the pressure in the chamber is reduced to about 150 mTorr. The primary drying cycle is complete when the formulation temperature was approximately −20°±2° C. for more than two hours. During the secondary drying process, the formulation is held at about −20° C. to about 10° C., preferably at a temperature above the primary drying cycle temperature, for about 40 to about 50 hours to facilitate secondary drying, i.e. removal of residual water and ethanol. When the partial pressures of water and ethanol in the chamber reaches a steady state, the drying is considered to be completed. These formulations provide a vacuum dried product which has been found to be a crystalline amifostine that demonstrates improved stability over the current formulation which contains amorphous amifostine. The vials can then be stored and shipped at temperatures from about 4° C. to about room temperature without significant product degradation.

Moreover, excipients can be added to increase the amount of solids present in the formulation. Among the excipients found useful for this purpose, often in combination, are sodium or potassium phosphates, sodium chloride, citric acid, tartaric acid, gelatin and carbohydrates such as dextrose, sucrose, sorbitol, inositol, mannitol and dextran. In addition to those mentioned herein others are known to those skilled in the art.

The vacuum dried crystalline amifostine solid compositions of the present invention may be provided in single dose container forms by aseptically filling suitable containers with the sterile pre-vacuum dried solution to a prescribed amifostine content; preparing the desired vacuum dried solid composition; and then hermetically sealing the single dose container. It is intended that these filled containers will allow rapid dissolution of the solid composition upon reconstitution with appropriate sterile diluents in situ giving an appropriate sterile solution of desired amifostine concentration for administration. As used herein, the term "suitable containers" means a container capable of maintaining a sterile environment, such as a vial, capable of delivering a vacuum dried product hermetically sealed by a stopper means. Additionally, suitable containers implies appropriateness of size, considering the volume of solution to be held upon reconstitution of the vacuum dried composition; and appropriateness of container material, generally Type I glass. The stopper means employed, e.g., sterile rubber closures or an equivalent, should be understood to be that which provides the aforementioned seal, but which also allows entry for the purpose of introduction of diluent, e.g., sterile Water for Injection, USP, Normal Saline, USP, or 5% Dextrose in Water, USP, for the reconstitution of the desired amifostine solution. These and other aspects of the suitability of containers for pharmaceutical products such as those of the instant invention are well known to those skilled in the practice of pharmaceutical arts.

While the physical properties, such as appearance, were improved in the instant solid compositions, thereby achieving one objective of the invention, we unexpectedly found that these instant solid compositions also possessed improved thermal stability compared with currently known formulation. In practice, expectation for enhancement of chemical stability by vacuum drying relates to a comparison of the stability of the vacuum dried solid with the stability of the solution form of the pharmaceutical composition. In contrast, the instant compositions demonstrate enhanced chemical stability between solid dosage forms, see Examples infra.

The pharmaceutical compositions of the present invention are suitable for parenteral administration, for example, intravenous, intramuscular, intracavitary, intrathecal, and subcutaneous injections.

The following examples are intended to be illustrative of the present invention and should not be construed, in any way, to be a limitation thereof.

EXAMPLES

Example 1: Procedure for Preformulation Studies

This example provides the procedure used for the preformulation studies which were designed to evaluate the appropriate parameters, i.e. amifostine concentration, ethanol concentration and temperature, for obtaining a sterile vacuum dried form of crystalline amifostine with and without pharmaceutically acceptable excipients using vacuum drying from a water/ethanol mixture.

A. Preparation of Sample Solutions

In separate test tubes with screw caps add the following:
(a) 5000 μL water
(b) 4750 μL water and 250 μL ethanol
(c) 4500 μL water and 500 μL ethanol
(d) 4250 μL water and 750 μL ethanol
(e) 4000 μL water and 1000 μL ethanol Add amifostine to each test tube until the solid remains undissolved. Sonicate for 30 seconds. If all the amifostine has dissolved, add an additional amount of drug substance until particles remain undissolved in the solvent. Vigorously shake the test tubes for 30 minutes at 25° C.

B. Preparation of Standard Solutions

Prepare 10 mL of the of the following solutions of Drug Substance in water:
(a) 0.05 mg/mL
(b) 0.1 mg/mL
(c) 0.3 mg/mL
(d) 0.5 mg/mL On a UV spectrophotometer, scan each solution against a water blank over a range of 190–290 nm. Record the absorbance at 200 nm or 210 nm. Perform linear regression analysis of standard data at 200 nm or 210 nm and obtain a slope and intercept value.

C. Analysis of Sample Solutions

Figure 2:
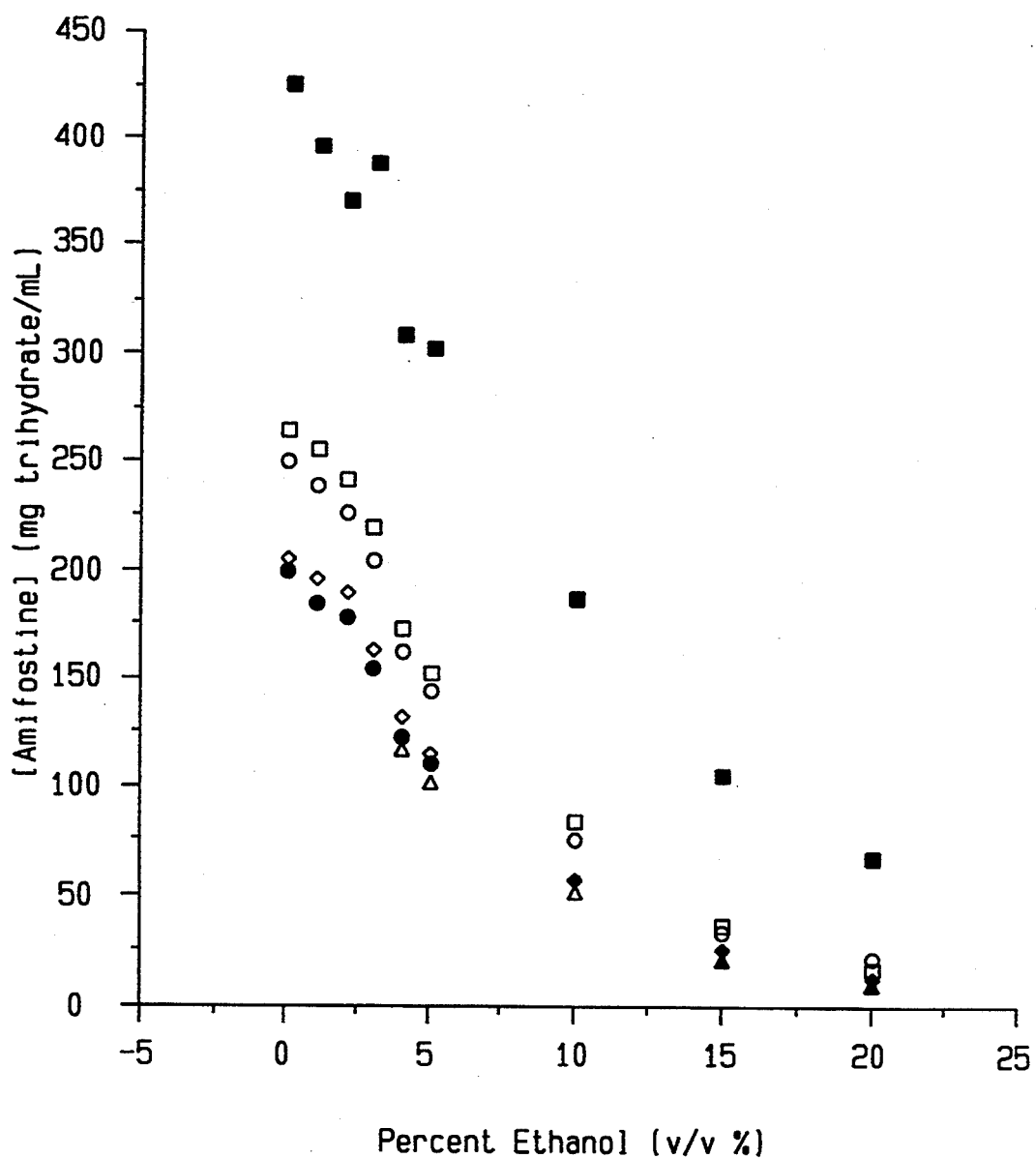
FIG. 2 Graph of the Dependence of Amifostine Drug Substance Solubility on Ethanol Concentration FIG. 3 TGA of Crystalline Amifostine Drug Product Formulated From 10% Ethanol in Water FIG. 4 TGA of Amifostine Drug Substance FIG. 5 DSC of Crystalline Amifostine Drug Product Formulated From 10% Ethanol in Water FIG. 6 DSC of Amifostine Drug Substance FIG. 7 FTIR of Crystalline Amifostine Drug Product Formulated From 10% Ethanol in Water FIG. 8 FTIR of Amifostine Drug Substance FIG. 9 X-ray Diffraction of Crystalline Amifostine Drug Product Formulated From 10% Ethanol in Water FIG. 10 X-ray Diffraction of Amifostine Drug Substance FIG. 11 TGA of Crystalline Amifostine and Mannitol Drug Product Formulated From 10% Ethanol in Water FIG. 12 DSC of Crystalline Amifostine and Mannitol Drug Product Formulated From 10% Ethanol in Water

Remove approximately 0.5 mL of each solution and centrifuge to pellet solids. Filter each sample with 0.45 μm filter to remove excess particles if necessary. Dilute each sample to a working concentration of 0.3 to 0.4 mg/mL with water. On the UV Spectrophotometer scan each sample over a range of 190–290 nm. Obtain a reading for each sample at 200 nm or 210 nm. From the standard slope and intercept and dilutions, calculate the concentration of amifostine in each solution. Cool the solutions to the next lowest temperature and repeat above after solution is at temperature for 1 hour. Table 1 provides the results of the solubility runs of amifostine in ethanol/water mixtures at various temperatures. This relationship is graphically demonstrated in FIGS. 1 and 2.

TABLE 1

| | Mean Solubility Amifostine Trihydrate in Ethanol/Water Mixtures (mg/mL) | | | | | |
|---|---|---|---|---|---|---|
| | 25° C. | 10° C. | 5° C. | 0° C. | −5° C. | −10° C. |
| Water | 425.7 | 264.0 | 251.2 | 204.7 | 199.8 | ND |
| 1% EtOH | 396.0 | 256.3 | 238.7 | 195.1 | 184.2 | ND |
| 2% EtOH | 370.9 | 241.7 | 226.6 | 189.6 | 177.2 | 186.1 |
| 3% EtOH | 389.0 | 220.4 | 204.7 | 162.4 | 154.1 | ND |
| 4% EtOH | 308.8 | 172.4 | 161.9 | 131.1 | 123.3 | 117.4 |
| 5% EtOH | 302.9 | 152.7 | 144.7 | 115.0 | 111.7 | 101.7 |
| 10% EtOH | 188.0 | 84.5 | 76.2 | 57.6 | 55.3 | 52.5 |
| 15% EtOH | 106.3 | 36.6 | 34.7 | 26.6 | 25.7 | 22.5 |
| 20% EtOH | 68.8 | 19.5 | 23.4 | 13.4 | 12.2 | 11.5 |

This example demonstrates that the solubility of amifostine drug substance is strongly dependent on both the ethanol co-solvent content and temperature. Generally, the degree of supersaturation resulting from a drop in the temperature of a given amifostine solution decreases with increasing ethanol co-solvent content (see Table 1 and FIGS. 1 and 2). This dependence is exploited in the following Examples 2 and 3 to achieve crystalline amifostine.

Example 2: Method of Producing Crystalline Amifostine Without Mannitol

To 130 mL of water at 25° C. add with stirring 21.25 gm of amifostine drug substance trihydrate, which is equivalent to 17.0 gm of anhydrous amifostine drug substance. After dissolution of amifostine drug substance is complete, 17 mL absolute ethanol, USP, is added to the solution with stirring. Water is then added to QS 170 mL. The resulting solution is sterile filtered through a 0.22 μm filter. To each of thirty-three 10 mL vials, is dispensed 5 mL of the filtered solution to give 500 mg amifostine, on an anhydrous basis, per vial in an ethanol:water ratio of 10:90. Split stoppers are placed on the vials and the samples are subjected to the following vacuum drying cycle: the samples are placed on the shelves of the freeze dryer, which has been pre-cooled to about −20° C., for about 17 hours at ambient pressure, after which time the chamber is evacuated and the shelves are held at about −20° C. for 28 hours. Following this period, the chamber is back-filled with nitrogen and the vials are quickly stoppered by hand. This procedure results in a thermally-stable, freeze-dried single dose vial containing approximately 500 mg of crystalline amifostine as an elegant cake.

Example 3: Method of Producing Crystalline Amifostine

Approximately 20 grams of mannitol is added with stirring to 150 mL of water at 25° C. To this solution is added, with stirring, approximately 25 grams amifostine drug substance (trihydrate basis), which is equivalent to 20 grams of anhydrous amifostine drug substance. After dissolution is complete, 20 mL of anhydrous ethanol, USP, is added volumetrically to the solution with stirring. Water is added QS to 200 mL. The resulting solution is sterile filtered through a 0.2 μm filter and 5 mL of solution is transferred to each of 40 10-mL vials. Split stoppers are placed on the vials and the samples are loaded onto the freeze-dryer shelf at ambient temperatures. The shelf temperature is decreased at 2° C./min to −25° C. and held at this temperature for 90 minutes to initiate amifostine crystallization. After this time, the shelf temperature is raised above the eutectic point at a rate of 2° C./min to −5° C. and held at this temperature for 10 hours to anneal the product. Subsequently, the shelf temperature is lowered to −25° C. until the product temperature is less than −18° C. for greater than 60 minutes. After this time, the freeze-dryer condenser is turned on and the vacuum in the chamber is lowered to 150 mTorr. The shelf-temperature is raised to −20° C. and the samples are allowed to vacuum dry for 14 hours. At this point, the monitored vials have reached shelf temperature, indicating the end of the primary drying cycle. The vials remain at 150 mTorr on the −20° C. shelf for an additional 13.4 hours to ensure the removal of non-hydrate water. The chamber is back-filled with nitrogen and the vials are mechanically stoppered. This procedure results in a thermally-stable, vacuum-dried single dose vial containing approximately 500 mg of amifostine (anhydrous basis) and 500 mg mannitol as an elegant cake.

Example 4: Vacuum Dried Crystalline Amifostine Stability Testing

Several sealed, nitrogen-filled vials of crystalline amifostine formulated from 10:90 ethanol:water, as described in Example 2 above, are stressed at 50° C. for up to 35 days to determine the thermal stability of the crystalline amifostine.

The results are tabulated in Table 2 below. All data are reported as percent (%) of initial concentration, which is defined as 100%.

TABLE 2

| STUDY | TIME AT 50° C. (IN DAYS) | % OF INITIAL CONCENTRATION |
| --- | --- | --- |
| 1 | 0 | 100.0 |
|   | 3 | 106.3 |
|   | 35 | 96.9 |
| 2 | 0 | 100.0 |
|   | 3 | 97.2 |
|   | 7 | 101.1 |
|   | 14 | 93.9 |
|   | 21 | 71.1 |
| 3 | 0 | 100.0 |
|   | 3 | 103.6 |
|   | 7 | 101.8 |
|   | 14 | 97.5 |
|   | 21 | 86.7 |

For comparison purposes, the current amorphous amifostine formulation is also subjected to stress testing at 50° C. for up to 28 days. The results are presented in Table 3 below. All data are reported as percent (%) of initial concentration, which is defined as 100%.

TABLE 3

| STUDY | TIME AT 50° C. (IN DAYS) | % OF INITIAL CONCENTRATION |
| --- | --- | --- |
| 1 | 0 | 100.0 |
|   | 14 | 2.8 |
|   | 28 | 1.5 |
| 2 | 0 | 100.0 |
|   | 14 | 2.0 |
|   | 28 | 1.4 |
| 3 | 0 | 100.0 |
|   | 14 | 1.7 |
|   | 28 | 1.4 |

Hence, it is abundantly clear that, even between solid formulations, a dramatic increase in thermal stability is achieved by crystalline compositions obtained from the disclosed process.

Example 5: Preferred Method of Producing Crystalline Amifostine

Compounding Procedure for Amifostine/Mannitol (100 mg anydrous each/mL)

The following procedure was written to yield 3.5 liters of solution.

1. 350 grams mannitol (USP) were dissolved with stirring (magnetic teflon stir bar) in about 2300 mL Nanopure water at room temperature in a stainless steel pressure vessel.
2. 438.3 grams amifostine trihydrate was added to this solution. Dissolution was aided with vigorous stirring.
3. After amifostine dissolution were complete, 525 mL dehydrated ethanol (USP) was slowly added to the solution with vigorous stirring. Amifostine precipitation occurs at the addition site followed by rapid re-dissolution as the ethanol is diluted by stirring.
4. After the addition of the ethanol is complete, the solution was diluted to 3500 mL with Nanopure water.
5. The solution was filtered under a positive pressure of 10 psi (nitrogen) through a Millipore-40 filter.
6. 5 mL of the resulting solution was transferred to each of 660 10-mL tubing vials (Wheaton E-2910-B47B). The vials were partially seated with grey butyl rubber stoppers (Tompkins PT23B0857 F2) and vacuum dried.

Vacuum drying Cycle for Amifostine/Mannitol (100 mg anhydrous/mL)

1. Vials are placed on the shelf at about 25° C. to insure that amifostine precipitation is not initiated heterogeneously.
2. The shelf temperature is lowered at 2° C. per minute to −35° C. Once this shelf temperature is obtained, it is held constant for 240 minutes to insure solution freezing of all vials. During this stage the samples pass through a eutectic (approximately −16° C.).
3. At the end of the 240 minute hold time, the shelf temperature is raised at 2° C. per minute to 0° C. over 25 minutes. Once this shelf temperature is obtained, it is held constant for 600 minutes.
4. At the end of the 600 minute hold time, the shelf temperature is again lowered to −35° C. at 2° C. per minute. Once this temperature is obtained, it is held constant for 180 minutes.
5. After this time, the condenser is turned on. When the condenser temperature is less than −40° C., the chamber is evacuated. When the chamber pressure is less than 150 mT, the shelf temperature is raised to −20° C. at 2° C. per minute and the chamber pressure is held at 150 mT with a nitrogen chamber bleed.
6. The product is left in the chamber at 150 mT for 12 to 24 hours after the monitored product temperature has reached shelf temperature. The chamber is back-filled with nitrogen and the vials stoppered.

NOTE: 1 Torr is equivalent to 1 millimeter of Hg at 0° C.

Sealed, nitrogen-filled 10 ml tubing vials containing vacuum dried crystalline amifostine, obtained as described in Example 5, were stressed at 40° C. for 4 weeks. For crystalline amifostine dried at −20° C. for 12 hours, 93% of the amifostine remained at the end of the stress test period. For cystalline amifostine dried at −20° C. for 24 hours, 84% of the amifostine remained at the end of the stress test period.

Example 6: Most Preferred Method of Producing Crystalline Amifostine

It was found that the most stable vacuum dried, crystalline amifostine was obtained by vacuum-drying an amifostine/mannitol, ethanol/water solution containing 15% v/v ethanol. The compound procedure is the same as described in Example 5 except for the lesser amount of dehydrated ethanol added to the solution.

The specific manner of conducting the vacuum drying cycle to produce the most stable crystalline amifostine was arrived at after several studies were performed to evaluate effects of changing the final drying temperature, the time period for final drying, and the rate of initial cooling to −35° C. of the solution-containing vials. It was found that in general, the stability of crystalline amifostine is the greatest when the final drying temperature was at −20° C., and the time for the final drying was between 12 and 24 hours. Additionally, the stability of the crystalline amifostine was higher when the initial cooling to −35° C. of the solution-containing vials was conducted in 160 minutes rather then 45 minutes.

Based on the above development studies, the most preferred manner of conducting the vacuum drying cycle is as follows:

Vacuum drying Cycle for Amifostine/Mannitol (100 mg anhydrous/mL)

1. Vials are placed on the shelf at about 25° C. to insure that amifostine precipitation is not initiated heterogeneously.
2. The shelf temperature is lowered from 25° C. to 0° C. in 20 minutes, 0° to −20° C. in 60 minutes, and then from −20° C. to −35° C. in 80 minutes. Once the shelf temperature is obtained, it is held constant for 240 minutes to insure solution freezing of all vials. During this stage the samples pass through a eutectic (approximately −16° C.).
3. At the end of the 240 minute hold time, the shelf temperature is raised to 0° C. over 25 minutes. Once the shelf temperature of 0° C. is obtained, it is held constant for 600 minutes.
4. At the end of the 600 minute hold time, the shelf temperature is again lowered from 0° C. to −15° C. in 15 minutes, and then from −15° C. to −35° C. in 120 minutes. Once the temperature of −35° C. is obtained, it is held constant for 180 minutes.
5. After this time, the condenser is turned on. When the condenser temperature is less than −40° C., the chamber is evacuated. When the chamber pressure is less than 150 mT, the shelf temperature is raised from −35° C. to −20° C. at 2° C. per minute while the chamber pressure is held at 150 mT with a nitrogen chamber bleed.
6. The product in the vials is left in the chamber at 150 mT for 12 to 24 hours after the monitored product temperature has reached shelf temperature. The chamber is back-filled with nitrogen and the vials stoppered.

NOTE: 1 Torr is equivalent to 1 millimeter of Hg at 0° C.

Without wishing to be limited by theory, it is believed that above step 2 causes the formation of seed crystals of amifostine in the frozen solution and step 3 causes the growth of amifostine crystals around the seed crystals and ensures completion of the crystallization of amifostine from the partially frozen solution.

Crystalline amifostine has been produced using the above vacuum drying cycle, utilizing 12.5% ethanol solution—one produced with a final drying step of 12 hours and another produced with a final drying step of 24 hours. Stress testing of these two products at 40° C. for eight weeks indicate no perceptible decomposition of amifostine for the product dried for 12 hours, and a 2% decomposition of amifostine for the product dried for 24 hours.

Example 7: Preferred Manner of Conducting Crystalline Amifostine Stability Testing Sealed, nitrogen-filled 10 ml tubing vials containing vacuum dried crystalline amifostine, obtained as described in Example 6, were stressed at 40° C. for up to eight weeks.

It was found that previous stability testing at 50° C. caused decomposition of the crystalline amifostine in the sealed vials in a manner not easily correlated to the stability of the crystalline amifostine under typical storage conditions (i.e. at refrigeration temperature of about 4° C.). However, results of stability testing at 40° C. and less can be correlated to the stability of crystalline amifostine under typical storage conditions. As an approximation, stability for one month at 30° C. correlates to eighteen months at 4° C.; stability for 2-3 weeks at 40° C. correlates to 18 months at 4° C.; and stability for 8-12 weeks at 40° C. correlates to 18 months at 25° C.

See L. Lachman, et al. The Theory and Practice of Industrial Pharmacy pages 766–67 for a general discussion of stability prediction.

At the end of the stress period, the crystalline amifostine in the vials was tested for water content, thiol content, and amifostine content. The water content was determined by Karl Fischer titration. Because amifostine may undergo hydrolysis under stress to produce 2-[(3-aminopropyl)amino] ethane thiol and phosphoric acid, determination of the amount of this thiol gives an indication of the stability of the amifostine. Analysis of thiol and amifostine content was conducted using the following procedure:

1. Preparation of Standards and Samples

Weight and volumes may be adjusted provided the final concentrations remain the same. Store solutions under refrigeration and/or in a refrigerated autosampler immediately after preparation.

1.1 Preparation of Amifostine Standard solutions (3 mg/mL, Methanol/Water [50/50])

Accurately weigh approximately 30.0 mg of amifostine standarded into a 10-mL volumetric flask. Dissolve in 5 mL of water and dilute to volume with methanol.

Shelf-Life: 24 hours at 4° C.

1.2 Preparation of 2-[(3-amino propyl)amino] ethanethiol, dihydrochloride Standard Solution (0.012 mg/mL Free Base, Methanol/Water [50/50])

Accurately weigh approximately 1.85 mg of 2-[(3-amino propyl)amino] ethanethiol, dihydrochloride standard into a 100-mL volumetric flask. Add 50 mL of water then dilute to volume with methanol.

Shelf-Life: 24 hours at 4° C.

1.3 Preparation of Amifostine (Drug Substance)

A. Assay Preparation (3 mg/mL, Methanol/Water [50/50])

Accurately weigh approximately 30.0 mg of amifostine into a 10-mL volumetric flask. Dissolve in 5 mL of water and dilute to volume with methanol.

Shelf-Life: 24 hours at 4° C.

B. Related Substances (15 mg/mL, Water)

Accurately weigh approximately 150.0 mg of amifostine into a 10-mL volumetric flask. Dissolve and dilute to volume with water.

Shelf-Life: 24 hours at 4° C.

1.4 Preparation of Amifostine for Injection (Drug Product) (4.8 mg/mL, Methanol/Water [50/50])

Dissolve contents of one drug product vial with about 9 mL water.

Quantitatively transfer sample to 25 mL volumetric flask and dilute to volume with water. Transfer 6 mL of this solution to a 50-mL volumetric flask, add 19 mL of water and dilute to volume with methanol.

Shelf-Life: 24 hours at 4° C.

2. System Suitability

| Amifostine (Use Standard Solution 1.1) | |
|---|---|
| % RSD of 6 Replicate Injection of Amifostine | ≦2 |
| Tailing Factor | ≦2 |
| Theoretical Plates | >1,000 |

| 2-[(3-aminopropyl)amino] ethanethiol, dichloride ("WR-1065") (Use Standard Solution 1.2) | |
|---|---|
| % RSD of 6 Injections | ≦4 |
| Tailing Factor | ≦2 |
| Theoretical Plates | >7,000 |

3. Equipment and Materials (As Stated Below or Equivalent)

Equipment
HPLC System with UV Detector
Materials
Amifostine Standard
Concentrated Phosphoric Acid (H$_3$PO$_4$): HPLC Grade
Methanol (MeOH): HPLC Grade
Purified Water: 16 meg-ohm or greater
1-Octanesulfonic Acid, Sodium Salt (OSA): HPLC Grade
HPLC Chromatographic Conditions
Column Specifications:
  Packing Material: TosoHaas TSK ODS-80TM, end-capped (USP L1)
  Dimensions: 4.6×250 mm
  Particle Size: 5 μm
    Mobile Phase: Methanol/Aqueous Phosphoric Acid, pH 3.0, 3.5 mM OSA (50/50)
      1. Dissolve 0.38 g OSA in 500 mL of aqueous phosphoric acid pH 3.0
      2. Dilute to 1000 mL with methanol.
      3. Filter and degas the mobile phase.
Detection: 220 nm Absorbance
Flow Rate: 1.0 mL/min
Injection Volume: 10 μL
Column Temperature: Ambient
Sample Temperature: 4° C.
Attenuation: Adjust to produce approximately 80% full-scale amifostine peak.

4. Procedure

Inject sample and standard solutions, record retention time of the amifostine peak (approximately 4 minutes). Retention time of the standard amifostine peak and the sample preparation peak should agree within 10% to confirm identification of amifostine in the sample.

5. Calculations

Assay Amifostine

Amifostine (% w/w) =

$$\frac{\text{Area Sample}}{\text{Area Standard}} \times \frac{\text{Wt. Standard (mg)}}{\text{Wt. Sample (mg)}} \times P \times 100$$

$$P = \frac{\% \text{ Purity of Standard}}{100}$$

Assay Amifostine for Injection

Amifostine(anhydrous) % Label Claim =

$$\frac{\text{Area Sample}}{\text{Area Standard}} \times \frac{\text{Wt. Standard (mg)}}{10 \text{ mL}} \times P \times F$$

$$F = \frac{(50 \text{ mL}) (25 \text{ mL})}{(6 \text{ mL}) (500 \text{ mg/vial})} \times 100 = 41.67$$

WR-1065

$$\% \text{ WR-1065 in Amifostine} = \frac{\text{Area WR-1065 Sample}}{\text{Area WR-1065 Standard}} \times$$

$$\frac{\text{Wt. WR-1065 Standard (mg)}}{\text{Wt. of Amifostine (mg)}} \times P \times F \frac{134.25}{207.16}$$

$$F = \frac{10 \text{ mL}}{100 \text{ mL}} \times 100 = 10$$

$$\frac{\% \text{ WR-1065 in}}{\text{Amifostine for Injection}} = \frac{\text{Area WR-1065 Sample}}{\text{Area WR-1065 Standard}} \times$$

$$\frac{\text{Wt. WR-1065 Standard (mg)}}{100 \text{ mL}} \times P \times F \frac{134.25}{207.16}$$

$$F = \frac{(50 \text{ mL}) (25 \text{ mL})}{(6 \text{ mL}) (500 \text{ mg/vial})} \times 100 = 41.67$$

RelatedSubstances (RS)

Exclude peaks on the related substance sample chromatogram which are found on the blank chromatogram or peaks from solvent front disturbances.

For each additional related substance detected, report the relative peak area percent:

$$\frac{\text{Individual Related}}{\text{Substance \%}} = \frac{\text{Peak Area (RS)}}{\text{Total Peak Area}} \times 100$$

Report the WR-1065 percentage and any additional related substance greater than 0.1% area.
Report the total of all the related substance.

Example 8: Stability Results of Vacuum Dried, Crystalline Amifostine Stressed at 40° C.

Typical results obtained by stressing crystalline amifostine produced by the method described in Example 6 and tested as described in Example 7 is summarized in Table 4.

TABLE 4

| | Stability Results of vacuum dried, crystalline amifostine at 40° C. | | |
|---|---|---|---|
| Time Acceptance Criteria | % H2O 10–14% w/w | % Thiol NMT 2.0% w/w | % Amifostine 38–46% w/w |
| | Lot 812 | | |
| Initial | 12.1 | 0.5 | 44.5 |
| 1 Week | 10.5 | 0.2 | 42.6 |
| 2 Weeks | 10.1 | 0.2 | 42.5 |
| 3 Weeks | 10.4 | 0.2 | 42.5 |
| 4 Weeks | 10.2 | 0.2 | 41.2 |
| 8 Weeks | 11.7 | 0.3 | 43.4 |
| | Lot 815 | | |
| Initial | 12.0 | 0.3 | 43.3 |
| 1 Week | 11.7 | 0.2 | 43.6 |
| 2 Weeks | 11.6 | 0.2 | 43.4 |
| 4 Weeks | 11.5 | 0.3 | 43.0 |

NMT = no more than

The above results clearly indicate the enhanced stability of the crystalline amifostine produced by the method described in Example 6. The enhanced stability is evident from the low weight percent of thiol formation, which indicates very little decomposition of the amifostine by hydrolysis to form 2-[(3-aminopropyl)amino] ethane thiol. Additionally, there is little loss in water content or amifostine content over time. This is in contrast to the poor stability of the vacuum dried amorphous amifostine formulation which exhibits significant decomposition within 14 days at 50° C. (See Table 3 of Example 4).

Example 9: Crystal Structure of Vacuum Dried Amifostine

The molecular and crystal structure of vacuum dried crystalline amifostine has been determined. Crystal survey, unit cell determination, and data collection were performed using copper radiation at room temperature.

The structure was solved by direct methods and refined by full-matrix least-squares and difference Fourier methods. All non-hydrogen atoms were refined anisotropically. The hydrogen atoms attached to the nitrogen and water oxygen atoms were located from difference Fourier maps and refined isotropically. The positions of the remaining hydrogen atoms were calculated assuming ideal geometries. These hydrogen atoms were not refined due to the low reflection to parameter ratio.

Figure 13:
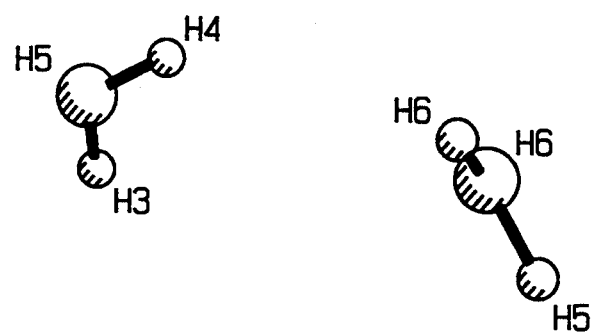
FIG. 13 depicts the molecular and crystal structure of vacuum dried amifostine
Figure 13:
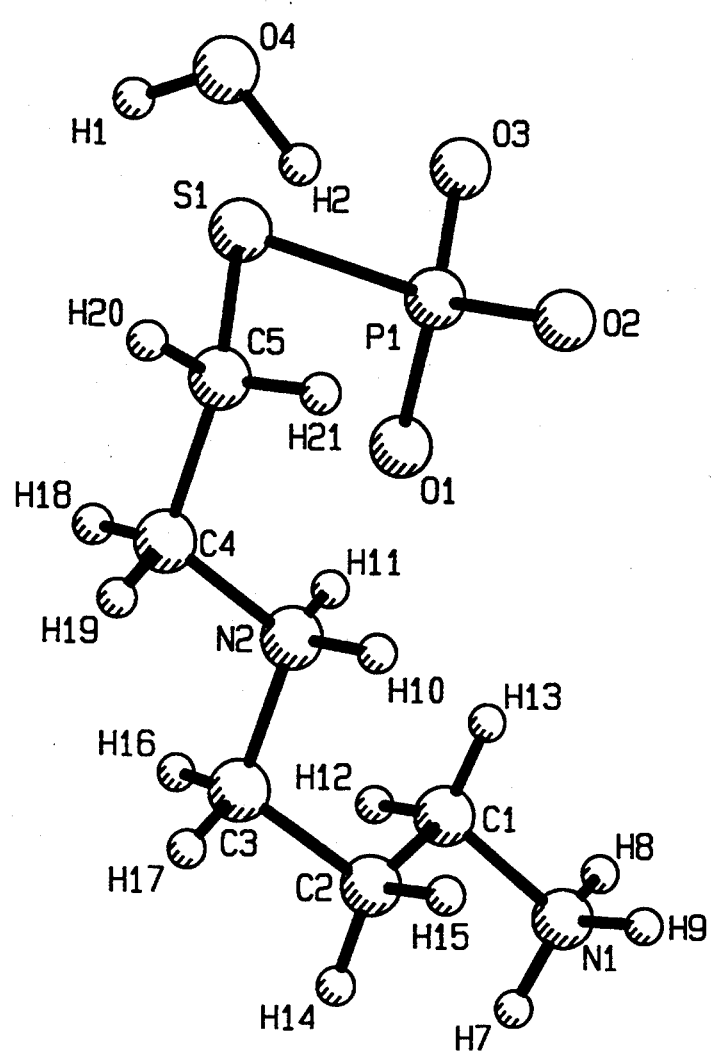

The compound crystallizes in the chiral space group $P2_12_12_1$. The data presented in this example are from the enantiomeric structure with lower R values (R=0.036 and $R_w$=0.042). The other enantiomeric structure has an R value of 0.042 and $R_w$ value of 0.051. A graphic depiction of the molecular and crystal structure of vacuum dried amifostine trihydrate is shown in FIG. 13.

Experimental

Data Collection

A colorless flat needle-shaped crystal of $C_5H_{21}N_2O_6PS$ having approximate dimensions of 0.350×0.050×0.030 mm was mounted on a glass fiber. All measurements were made on a Rigaku AFC5R diffractometer with graphite monochromated Cu Kα radiation and a 12 KW rotating anode generator.

Cell constants and an orientation matrix for data collection, obtained from a least-squares refinement using the setting angles of 20 carefully centered reflections in the range 40.45<2θ<52.03° corresponded to an orthorhombic cell with dimensions:

| | |
|---|---|
| a = | 8.456 (2)Å |
| b = | 21.553 (2)Å |
| c = | 6.758 (2)Å |
| V = | 1231.6 (5)Å³ |

For Z=4 and F. W.=268.26, the calculated density is 1.447 g/cm³. Based on the systematic absences of:

h00: h≠2n

0k0: k≠2n

00l: l≠2n and the successful solution and refinement of the structure, the space group was determined to be:

$P2_12_12_1$ (#19)

The data were collected at a temperature of 23°±1° C. using the ω-2θ scan technique to a maximum 2θ value of 120.0°. Omega scans of several intense reflections, made prior to data collection, had an average width at half-height of 0.21° with a take-off angle of 6.0°. Scans of (0.89+0.14 tan θ)° were made at a speed of 8.0°/min (in omega). The weak reflections (I<15.0-σ(I)) were rescanned (maximum of 4 rescans) and the counts were accumulated to assure good counting statistics. Stationary background counts were recorded on each side of the reflection. The ratio of peak counting time to background counting time was 2:1. The diameter of the incident beam collimator was 0.5 mm and the crystal to detector distance was 400.0 mm.

Data Reduction

A total of 1120 reflections was collected. The intensities of three representative reflections which were measured after every 150 reflections remained constant throughout data collection indicating crystal and electronic stability (no decay correction was applied).

The linear absorption coefficient for Cu Kα is 37.1 cm$^{-1}$. An empirical absorption correction, based on azimuthal scans of several reflections, was applied which resulted in transmission factors ranging from 0.89 to 1.00. The data were corrected for Lorentz and polarization effects.

Experimental Details

| EXPERIMENTAL DETAILS | |
|---|---|
| A. Crystal Data | |
| Empirical Formula | C$_5$H$_{21}$N$_2$O$_6$PS |
| Formula Weight | 268.26 |
| Crystal Color, Habit | colorless, flat needle |
| Crystal Dimensions (mm) | 0.350 × 0.050 × 0.030 |
| Crystal System | orthorhombic |
| No. Reflections Used for Unit Cell Determination (2θ range) | 20 (40.5–52.0°) |
| Omega Scan Peak Width at Half-height | 0.21 |
| Lattice Parameters: | a = 8.456 (2)Å |
| | b = 21.553 (2)Å |
| | C = 6.758 (2)Å |
| | V = 1231.6 (5)Å$^3$ |
| Space Group | P2$_1$2$_1$2$_1$ (#19) |
| Z value | 4 |
| D$_{calc}$ | 1.447 g/cm$^3$ |
| F$_{000}$ | 576 |
| μ(CuKα) | 37.10 cm$^{-1}$ |
| B. Intensity Measurements | |
| Diffractometer | Rigaku AFC5R |
| Radiation | CuKα (λ = 1.54178 Å) |
| Temperature | 23° C. |
| Attenuators | Zr (foil L factors: 3.8, 13.4, 47.8) |
| Take-off Angle | 6.0° |
| Detector Aperture | 6.0 mm horizontal |
| | 6.0 mm vertical |
| Crystal to Detector Distance | 40 cm |
| Scan Type | ω-2θ |
| Scan Rate | 8.0°/min (in omega) (4 rescans) |
| Scan Width | (0.89 + 0.14 tanθ)° |
| 2θ$_{max}$ | 120.0° |
| No. of Reflection Measured | Total: 1120 |
| Corrections | Lorentz-polarization |
| | Absorption |
| | (trans. factors: 0.89–1.00) |
| C. Structure Solution and Refinement | |
| Structure Solution | Direct methods |
| Refinement | Full-matrix least-squares |
| Function Minimized | Σ w (\|Fo\| − \|Fc\|)$^2$ |
| Least-squares Weights | 4Fo$^2$/σ$^2$(Fo$^2$) |
| p-factor | 0.03 |
| Anomalous Dispersion | All non-hydrogen atoms |
| No. Observations (I > 3.00σ(I)) | 856 |
| No. Variables | 180 |
| Reflection/Parameter Ratio | 4.76 |
| Residuals: R; R$_w$ | 0.036; 0.042 |
| Goodness of Fit Indicator | 1.37 |
| Max Shift/Error in Final Cycle | 0.00 |
| Maximum Peak in Final Diff. Map | 0.30 e$^-$/Å$^3$ |
| Maximum Peak in Final Diff. Map | −0.22 e$^-$/Å$^3$ |

| Positional parameters and B (eq) for C(5)H(21)N(2)O(6)P(1)S(1) | | | | |
|---|---|---|---|---|
| atom | x | y | z | B (eq) |
| S(1) | 0.5773(2) | 0.67451(7) | 0.3809(3) | 3.13(6) |
| P(1) | 0.5106(2) | 0.59073(6) | 0.2413(2) | 2.14(5) |
| O(1) | 0.3359(4) | 0.5965(2) | 0.1901(6) | 2.8(2) |
| O(2) | 0.5390(5) | 0.5383(2) | 0.3868(7) | 3.1(2) |
| O(3) | 0.6192(4) | 0.5882(2) | 0.0644(6) | 3.2(2) |
| O(4) | 0.8435(6) | 0.6830(3) | 0.970(1) | 4.7(3) |
| O(5) | 1.1634(7) | 0.7064(3) | 0.097(1) | 4.5(3) |
| O(6) | 1.2270(6) | 0.5451(2) | 0.8548(8) | 4.0(2) |
| N(1) | −0.1325(6) | 0.4983(2) | 0.2650(9) | 2.4(2) |
| N(2) | 0.2036(6) | 0.6289(2) | 0.5503(9) | 2.6(2) |
| C(1) | −0.0319(7) | 0.554(3) | 0.2978(9) | 2.8(3) |
| C(2) | −0.0611(7) | 0.5820(3) | 0.5004(9) | 2.9(3) |
| C(3) | 0.0296(7) | 0.6415(3) | 0.537(1) | 2.9(3) |
| C(4) | 0.2965(7) | 0.6853(3) | 0.604(1) | 3.0(3) |
| C(5) | 0.4721(7) | 0.6719(3) | 0.615(1) | 3.4(3) |
| H(1) | 0.796(8) | 0.716(3) | 0.94(1) | 4(1) |
| H(2) | 0.77(1) | 0.650(4) | 1.00(1) | 10(2) |
| H(3) | 1.08(1) | 0.699(4) | 0.04(1) | 6(2) |
| H(4) | 1.215(9) | 0.675(3) | 0.11(i) | 5(2) |
| H(5) | 1.147(8) | 0.521(3) | 0.87(1) | 4(1) |
| H(6) | 1.27(1) | 0.559(4) | 0.98(2) | 10(2) |
| H(7) | −0.24(1) | 0.513(3) | 0.28(1) | 4(1) |
| H(8) | −0.110(8) | 0.484(3) | 0.14(1) | 4(1) |
| H(9) | −0.104(8) | 0.466(3) | 0.34(1) | 4(1) |
| H(10) | 0.227(9) | 0.594(4) | 0.65(1) | 7(2) |
| H(11) | 0.234(7) | 0.617(2) | 0.443(9) | 2(1) |
| H(12) | −0.0561 | 0.5845 | 0.1998 | 3.4 |
| H(13) | 0.0763 | 0.5429 | 0.2873 | 3.4 |
| H(14) | −0.1709 | 0.5905 | 0.5130 | 3.4 |
| H(15) | −0.0306 | 0.5524 | 0.5974 | 3.4 |
| H(16) | 0.0103 | 0.6696 | 0.4318 | 3.5 |
| H(17) | −0.0052 | 0.6594 | 0.6582 | 3.5 |
| H(18) | 0.2787 | 0.7165 | 0.5077 | 3.6 |
| H(19) | 0.2617 | 0.6998 | 0.7299 | 3.6 |
| H(20) | 0.5188 | 0.7016 | 0.7010 | 4.1 |
| H(21) | 0.4852 | 0.6315 | 0.6694 | 4.1 |

It should be apparent to one of ordinary skill that other embodiments not specifically disclosed nonetheless fall within the scope and spirit of the present invention. Hence, the descriptions herein should not be taken as limiting the invention in any way, except as stated in the following claims.

What is claimed is:

1. A process for the preparation of a crystalline amifostine composition comprising the steps of:
    (a) preparing a formulation comprising amifostine, alcohol and water in which the relative amounts of amifostine, alcohol and water are such that a particulate-free solution is obtained at temperatures ranging from about room temperature to about 10° C., but which provides a crystalline precipitate of amifostine upon cooling below 0° C.;
    (b) cooling said formulation to a temperature below 0° C. for a period of time sufficient to effect the precipitation of the crystalline amifostine; and
    (c) vacuum drying the resulting mixture to leave a solid crystalline amifostine preparation having enhanced stability.

2. The process of claim 1 which further comprises introducing a sterile inert gas over said preparation after completion of the vacuum drying of step (c).

3. The process of claim 2 in which said inert gas is selected from the group consisting of argon, nitrogen and helium.

4. The process of claim 1 in which the temperature of step (b) is about a eutectic point of said formulation.

5. The process of claim 4 which further comprises, after step (b), raising the temperature of the resulting mixture to an annealing temperature that lies about 1° to about 20° C. above said eutectic temperature, followed by cooling the temperature of said mixture from said annealing temperature back to said eutectic temperature or below prior to performing step (c).

6. The process of claim 4 in which said eutectic temperature falls in the range of about 0° C. to about −80° C.

7. The process of claim 5 in which said annealing temperature falls in the range of about −30° C. to about 10° C. and said eutectic temperature falls in the range of about 0° C. to about −80° C.

8. The process of claim 1 in which said formulation comprises about 50 to about 400 mg amifostine per ml of formulation, about 1–35% (v/v) alcohol, and about 65–99% (v/v) water.

9. The process of claim 1 in which said formulation comprises about 125 to about 250 mg amifostine per ml of formulation, about 5–20% (v/v) alcohol, and about 80–95% (v/v) water.

10. The process of claim 1 in which said formulation comprises about 100 mg amifostine per ml of formulation, about 10% (v/v) alcohol, and about 90% (v/v) water.

11. The process of claim 1 in which said temperature of step (b) falls in the range of about −5° C. to about −40° C.

12. The process of claim 1 in which said temperature of step (b) is about −20° C.

13. The process of claim 1, which further comprises a sterilization step.

14. The process of claim 13 in which said sterilization step comprises sterile filtering said formulation of step (a) prior to cooling.

15. The process of claim 1, 4, 5 or 14 in which said crystalline amifostine is a hydrate of amifostine.

16. The process of claim 1, 4, 5 or 14 in which said crystalline amifostine is an amifostine trihydrate.

17. The process of claim 1, 4, 5 or 14 in which said crystalline amifostine contains from about 1 mole to about 3 moles of water of crystallization.

18. The process of claim 1, 4, 5 or 14 in which said formulation further comprises a pharmaceutically acceptable excipient.

19. The process of claim 18 in which said excipient is selected from the group consisting of sodium chloride, glycine, dextrose, sucrose and mannitol.

20. The process of claim 18 in which said excipient is mannitol.

21. A process for the preparation of a crystalline amifostine composition comprising the steps of:
(a) preparing a formulation comprising about 50 to about 300 mg amifostine per ml of said formulation, about 3 to about 30% (v/v) ethanol, about 70–97% (v/v) water, and, optionally, about 5 to about 300 mg of a pharmaceutically acceptable excipient per ml of said formulation such that a particulate-free solution is obtained at temperatures ranging from about room temperature to about 10° C. but which provides a crystalline precipitate of amifostine upon cooling below 0° C.;
(b) cooling said formulation to a temperature falling in the range of about −5° C. to about −40° C. for a period of time sufficient to effect the precipitation of the crystalline amifostine; and
(c) vacuum drying the resulting mixture to leave a solid crystalline amifostine preparation having enhanced stability.

22. The process of claim 1, 4, 5 or 21 in which the step(s) taken after step (a) and before step (c) are carried out over a period of about 0.5 to about 72 hours.

23. The process of claim 1, 4, 5 or 21 in which the step(s) taken after step (a) and before step (c) are carried out over a period of about 2 to about 24 hours.

24. The process of claim 1, 4, 5 or 21 in which step (c) is carried out over a period of about 1 to about 72 hours.

25. The process of claim 1, 4, 5 or 21 in which step (c) is carried out over a period of about 10 to about 20 hours.

26. The process of claim 1, 4, 5 or 21 in which step (c) is carried out at a vacuum of about 10 to about 1000 mTorr.

27. The process of claim 1, 4, 5 or 21 in which step (c) is carried out at a vacuum of about 150 mTorr.

28. The process of claim 1 wherein the alcohol is a $C_1$-$C_5$ alkyl alcohol.

29. The process of claim 1 wherein the alcohol is selected from the group consisting of methanol, ethanol, propanol, isopropanol, n-butanol, sec-butanol, tert-butanol, n-pentanol and 2-pentanol.

30. A process for the preparation of a crystalline amifostine composition comprising the steps of:
(a) preparing a formulation comprising about 100 mg amifostine per mL of said formulation, about 100 mg of a pharmaceutically acceptable excipient per mL of said formulation, and about 12.5% (v/v) ethanol in water solution such that a particulate free solution is obtained at about room temperature;
(b) cooling said formulation from room temperature to about −35° C. in about 160 minutes;
(c) maintaining said formulation at about −35° C. for about 240 minutes to form seeds of crystalline amifostine;
(d) warming said formulation to about 0° C. in about 25 minutes;
(e) maintaining said formulation at about 0° C. for about 600 minutes to anneal the seeds and precipitate crystalline amifostine;
(f) cooling said formulation from about 0° C. to about −15° C. in about 15 minutes;
(g) cooling said formulation from about −15° C. to about −35° C. in about 120 minutes;
(h) maintaining said formulation at about −35° C. for about 180 minutes;
(i) evacuating the air around said formulation to a pressure less than about 150 microns;
(j) warming said formulation from about −35° C. to about −20° C. over about 54 hours;
(k) maintaining said formulation at about −20° C. for about 12 to about 24 additional hours to leave a crystalline amifostine composition having enhanced stability.

31. Crystalline amifostine which is prepared according to the process of any of claims 1, 2, 4, 5, 7, 8, 9, 10, 21 or 30 and which is thermally-stable, sterile, and suitable for reconstitution with a pharmaceutically acceptable vehicle into an injectable particulate-free drug product for parenteral administration to a human patient.

32. Crystalline amifostine which is prepared according to the process of claim 13 and which is thermally-stable, sterile, and suitable for reconstitution with a pharmaceutically acceptable vehicle into an injectable particulate-free drug product for parenteral administration to a human patient.

33. Crystalline amifostine which is prepared according to the process of claim 18 and which is thermally-stable, sterile, and suitable for reconstitution with a pharmaceutically acceptable vehicle into an injectable particulate-free drug product for parenteral administration to a human patient.

* * * * *

UNITED STATES PATENT AND TRADEMARK OFFICE
CERTIFICATE OF CORRECTION

PATENT NO.        : 5,424,471
APPLICATION NO. : 08/099298
DATED             : June 13, 1995
INVENTOR(S)      : Kennedy et al.

Figure 3:
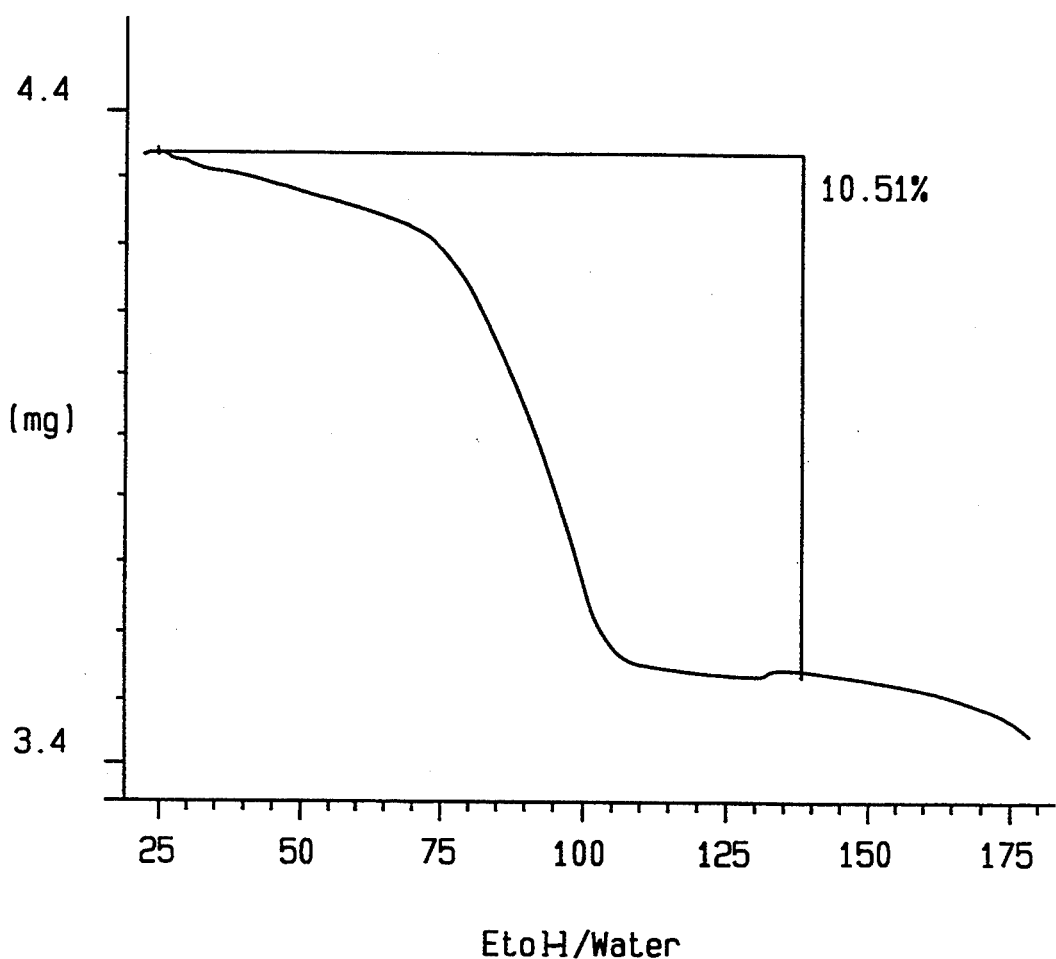

It is certified that error appears in the above-identified patent and that said Letters Patent is hereby corrected as shown below:

Fig. 3, should read

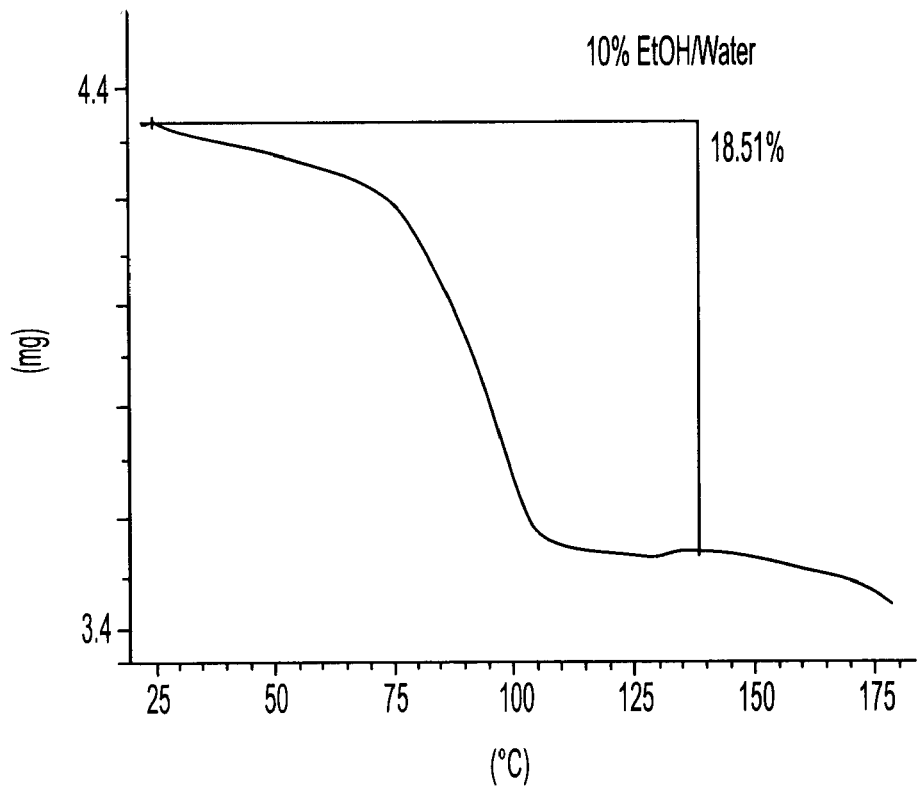

Fig. 3

UNITED STATES PATENT AND TRADEMARK OFFICE
CERTIFICATE OF CORRECTION

PATENT NO. : 5,424,471
APPLICATION NO. : 08/099298
DATED : June 13, 1995
INVENTOR(S) : Kennedy et al.

Figure 4:
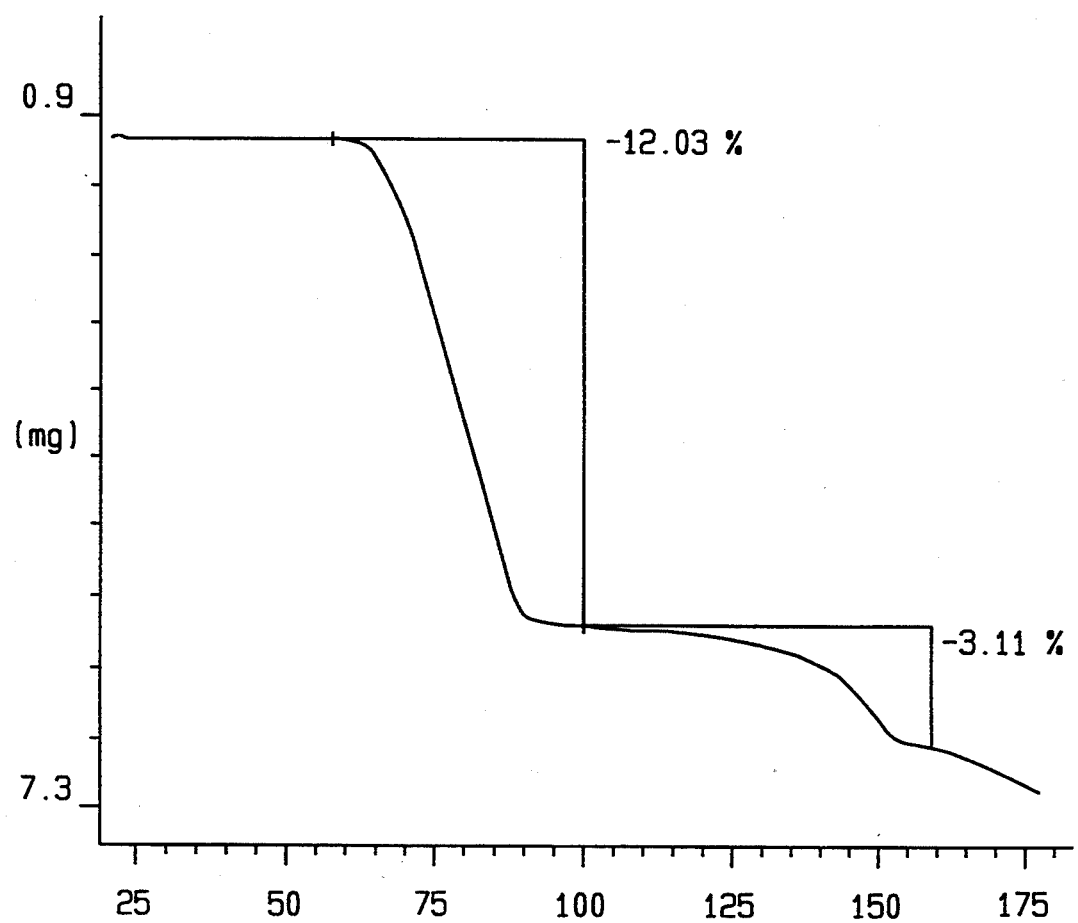

It is certified that error appears in the above-identified patent and that said Letters Patent is hereby corrected as shown below:

Fig. 4, should read

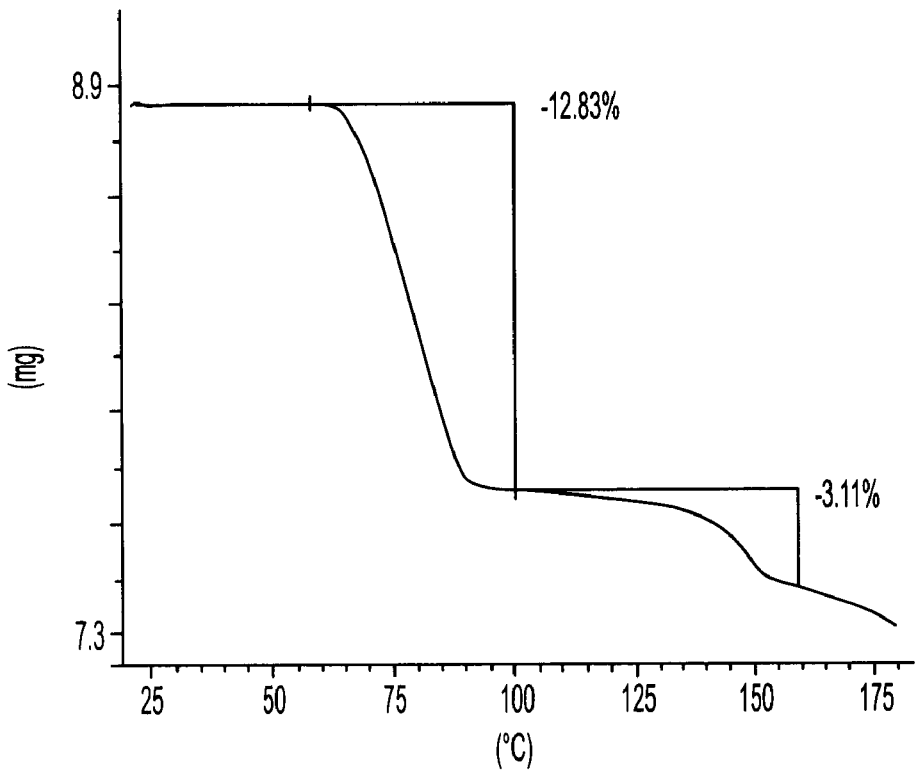

Fig. 4

UNITED STATES PATENT AND TRADEMARK OFFICE
CERTIFICATE OF CORRECTION

PATENT NO.      : 5,424,471                                  Page 3 of 8
APPLICATION NO. : 08/099298
DATED           : June 13, 1995
INVENTOR(S)     : Kennedy et al.

It is certified that error appears in the above-identified patent and that said Letters Patent is hereby corrected as shown below:

Fig. 5 should read

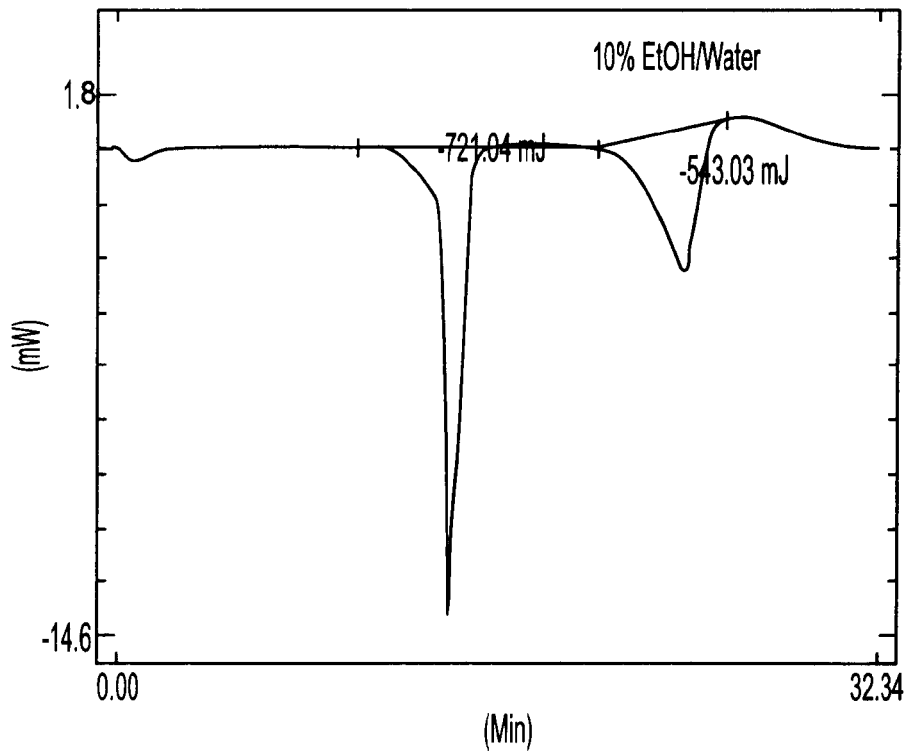

Figure 5:
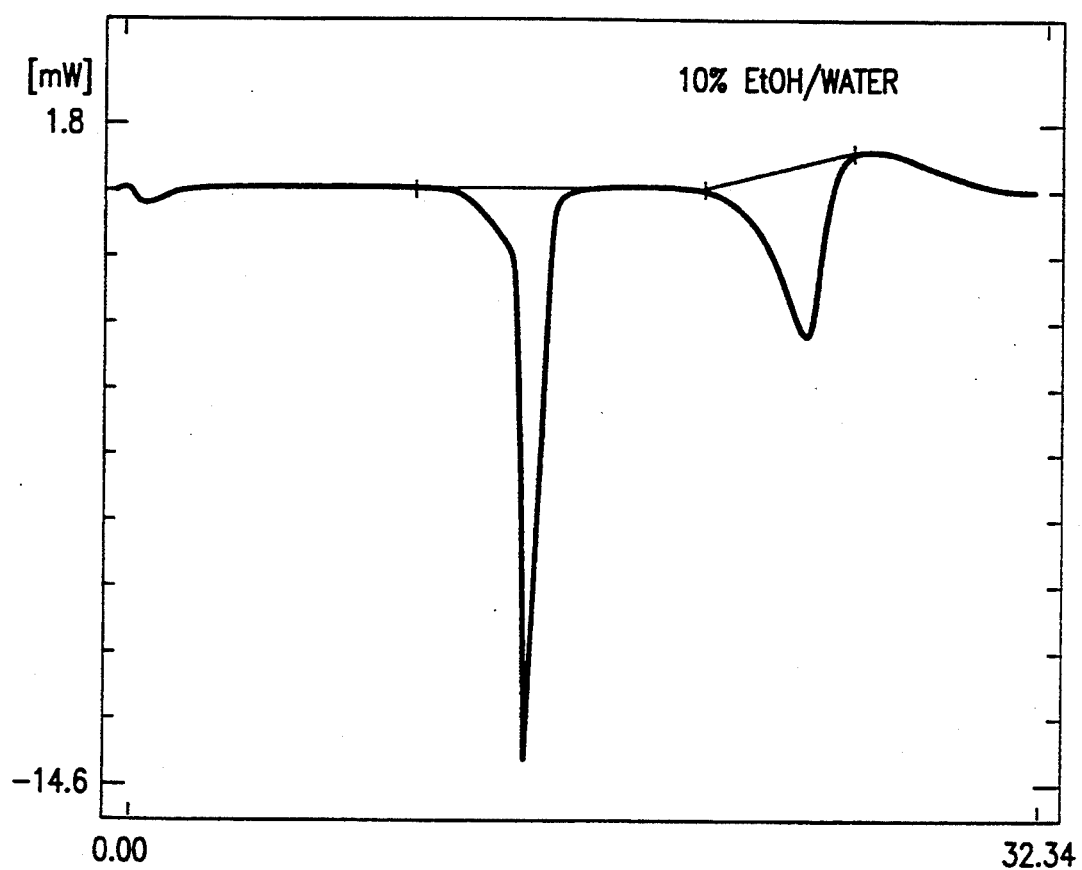

*Fig. 5*

UNITED STATES PATENT AND TRADEMARK OFFICE
CERTIFICATE OF CORRECTION

PATENT NO.        : 5,424,471
APPLICATION NO.   : 08/099298
DATED             : June 13, 1995
INVENTOR(S)       : Kennedy et al.

Page 4 of 8

Figure 6:
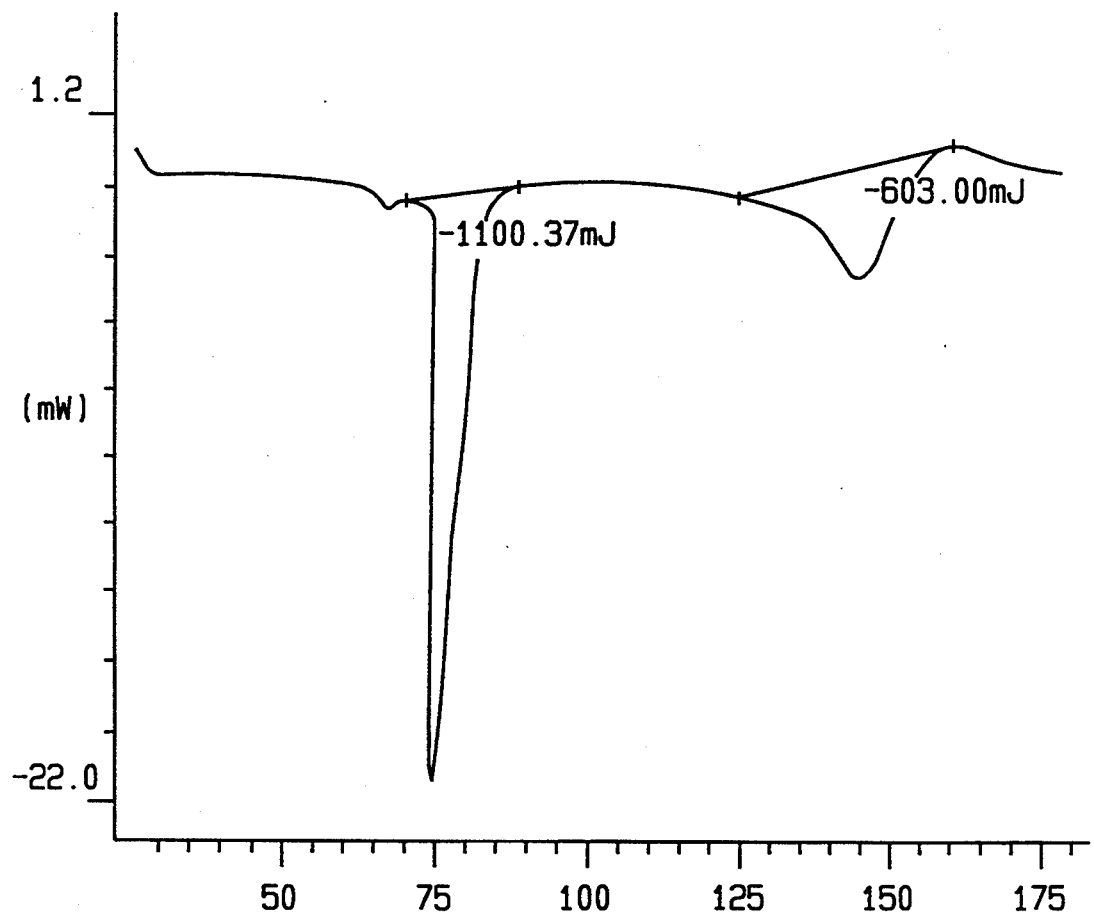

It is certified that error appears in the above-identified patent and that said Letters Patent is hereby corrected as shown below:

Fig. 6, should read

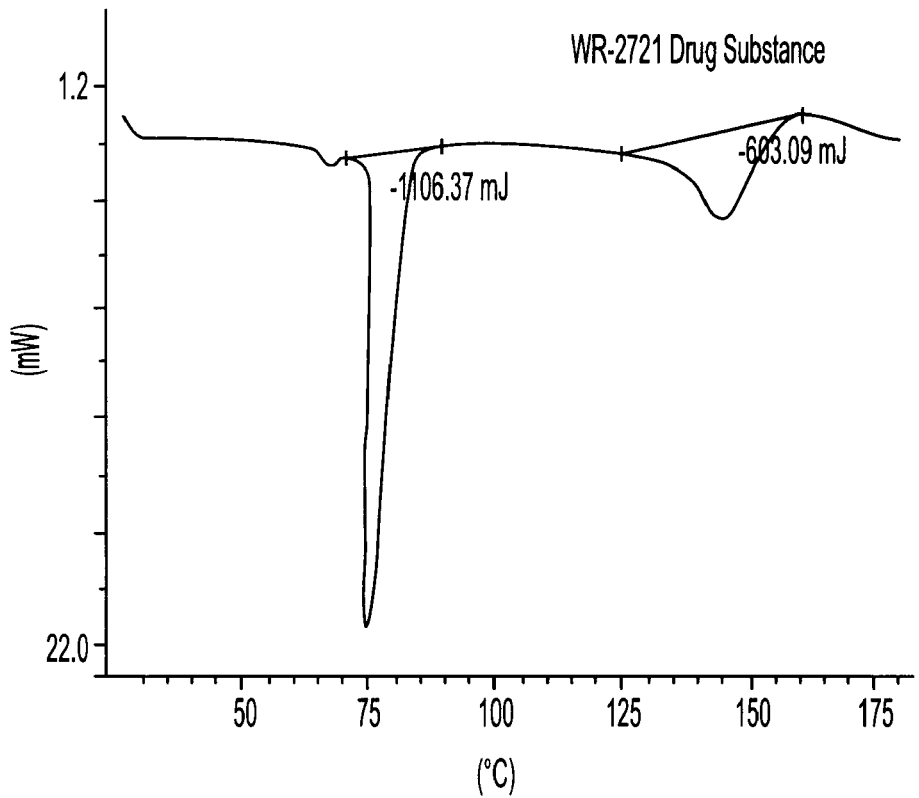

Fig. 6

UNITED STATES PATENT AND TRADEMARK OFFICE
CERTIFICATE OF CORRECTION

PATENT NO. : 5,424,471  
APPLICATION NO. : 08/099298  
DATED : June 13, 1995  
INVENTOR(S) : Kennedy et al.

Figure 7:
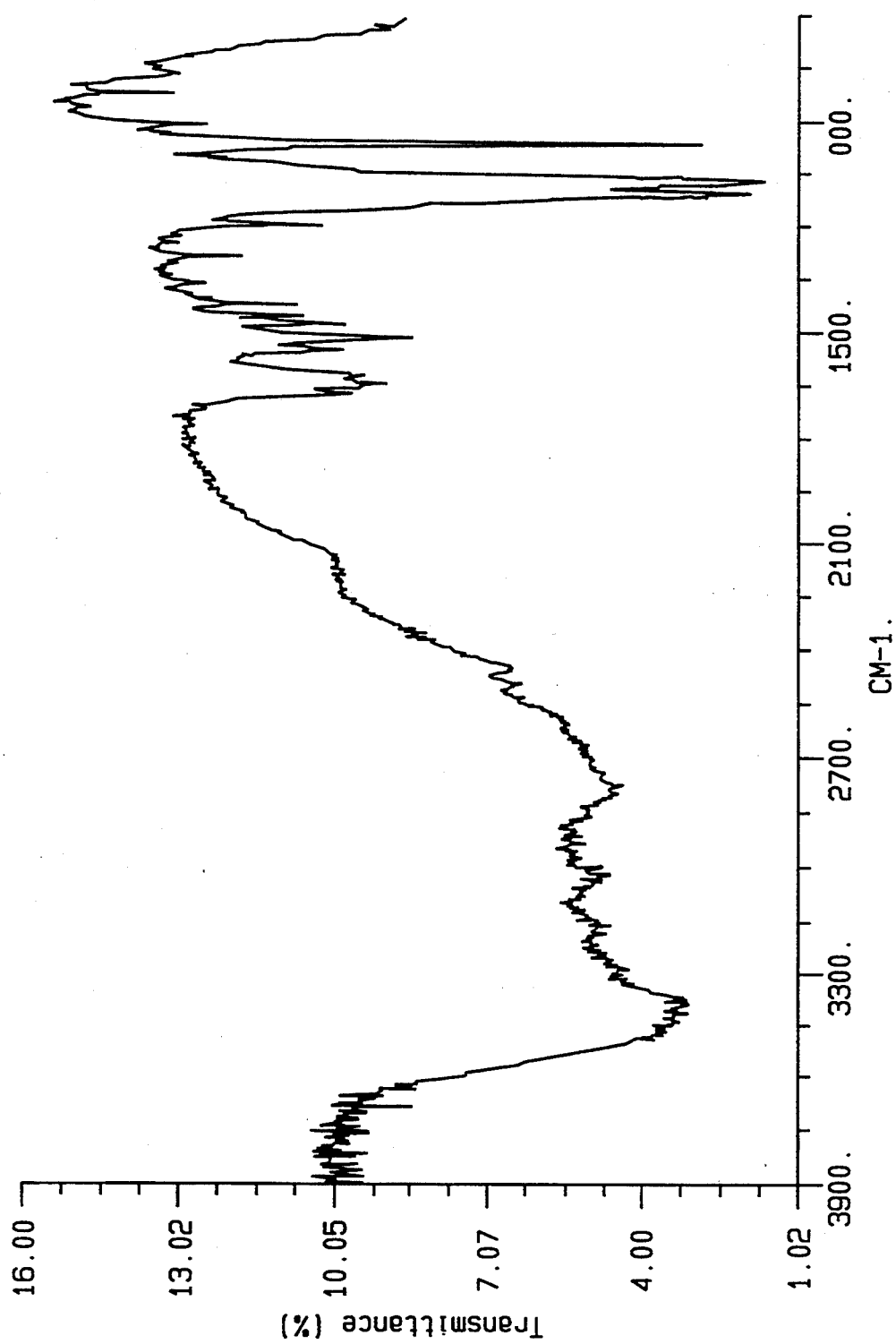

It is certified that error appears in the above-identified patent and that said Letters Patent is hereby corrected as shown below:

Fig. 7, should read

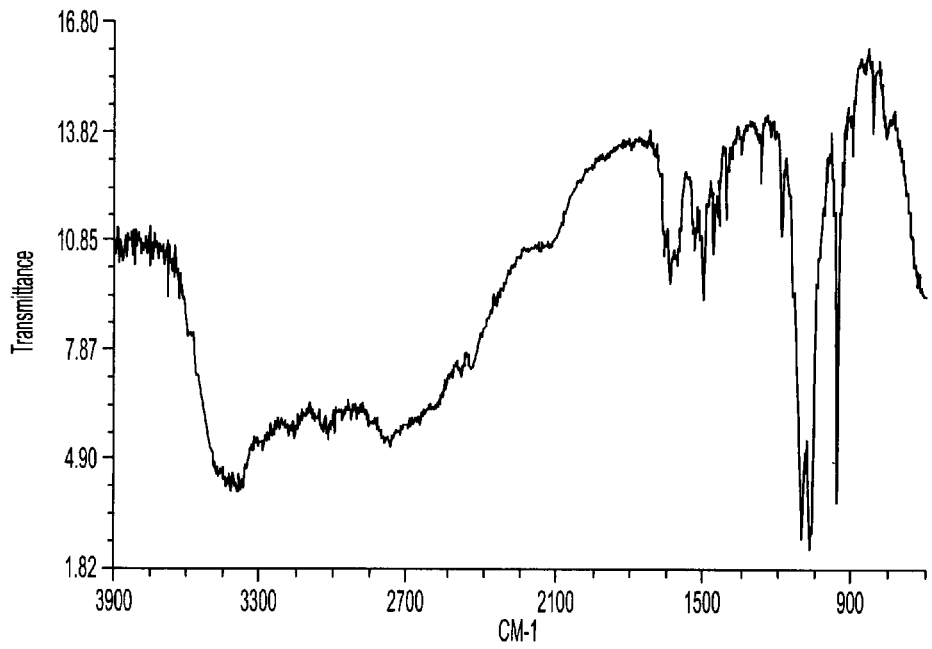

Fig. 7

UNITED STATES PATENT AND TRADEMARK OFFICE
CERTIFICATE OF CORRECTION

PATENT NO. : 5,424,471
APPLICATION NO. : 08/099298
DATED : June 13, 1995
INVENTOR(S) : Kennedy et al.

Figure 8:
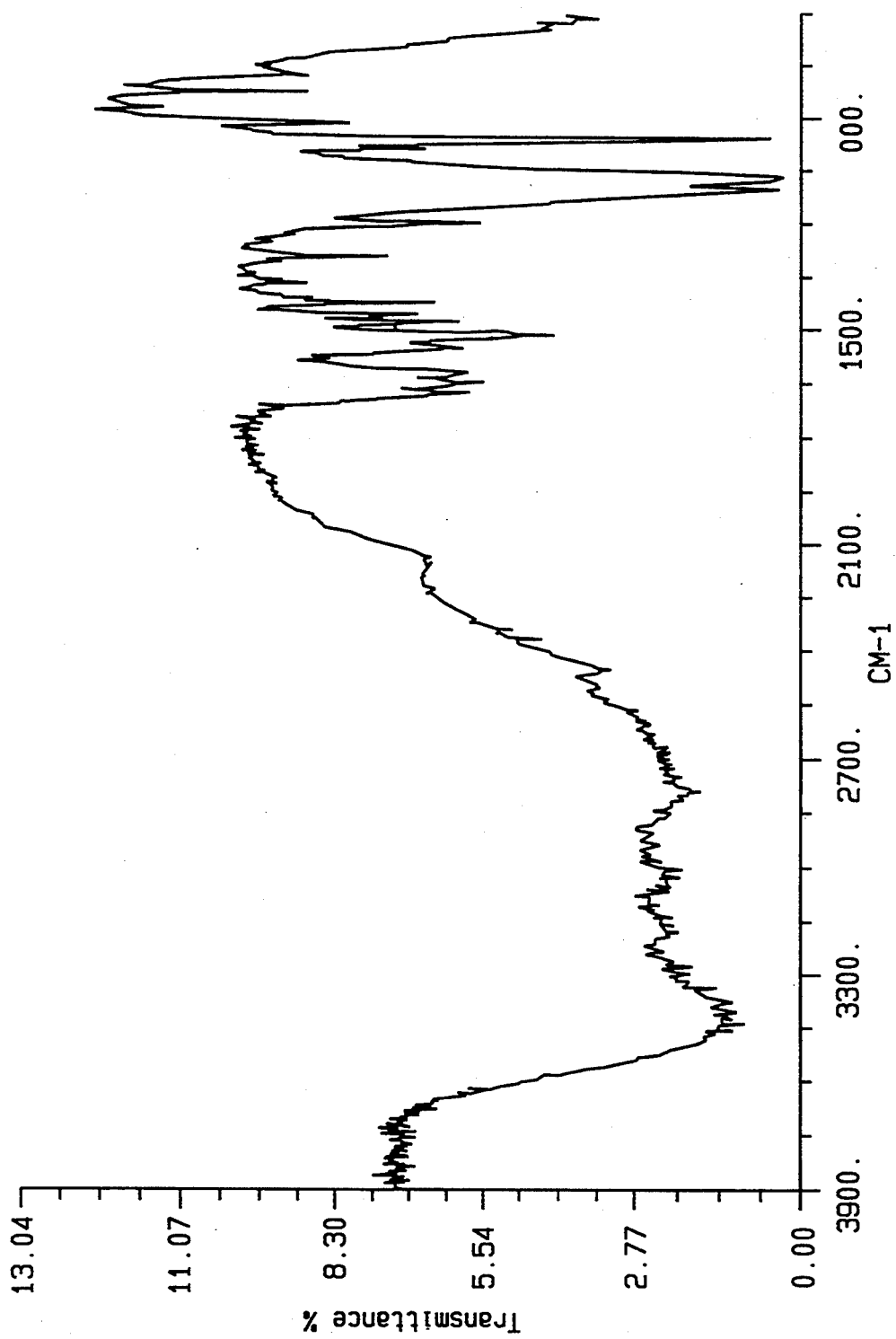
Figure 9:
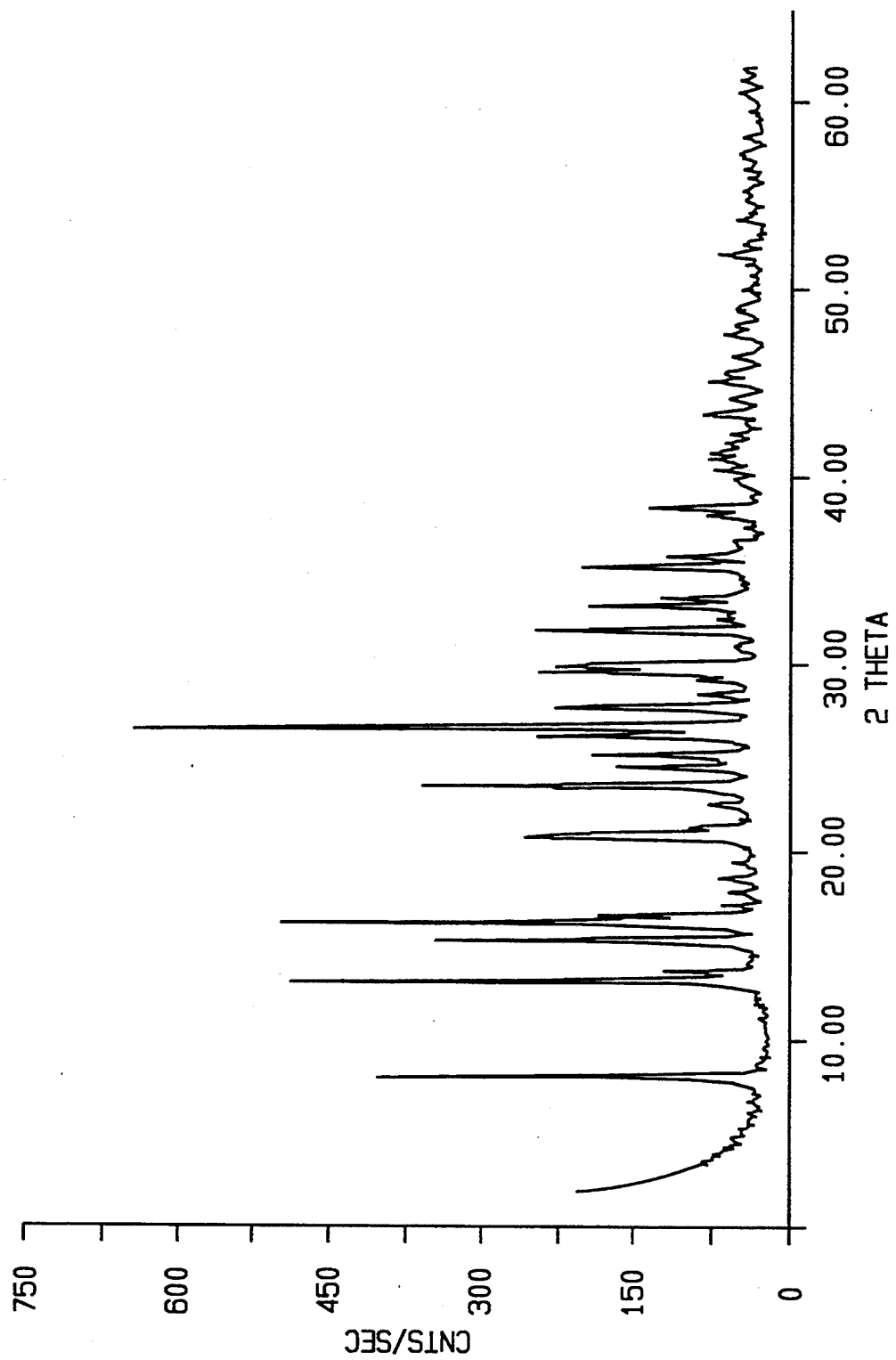
Figure 10:
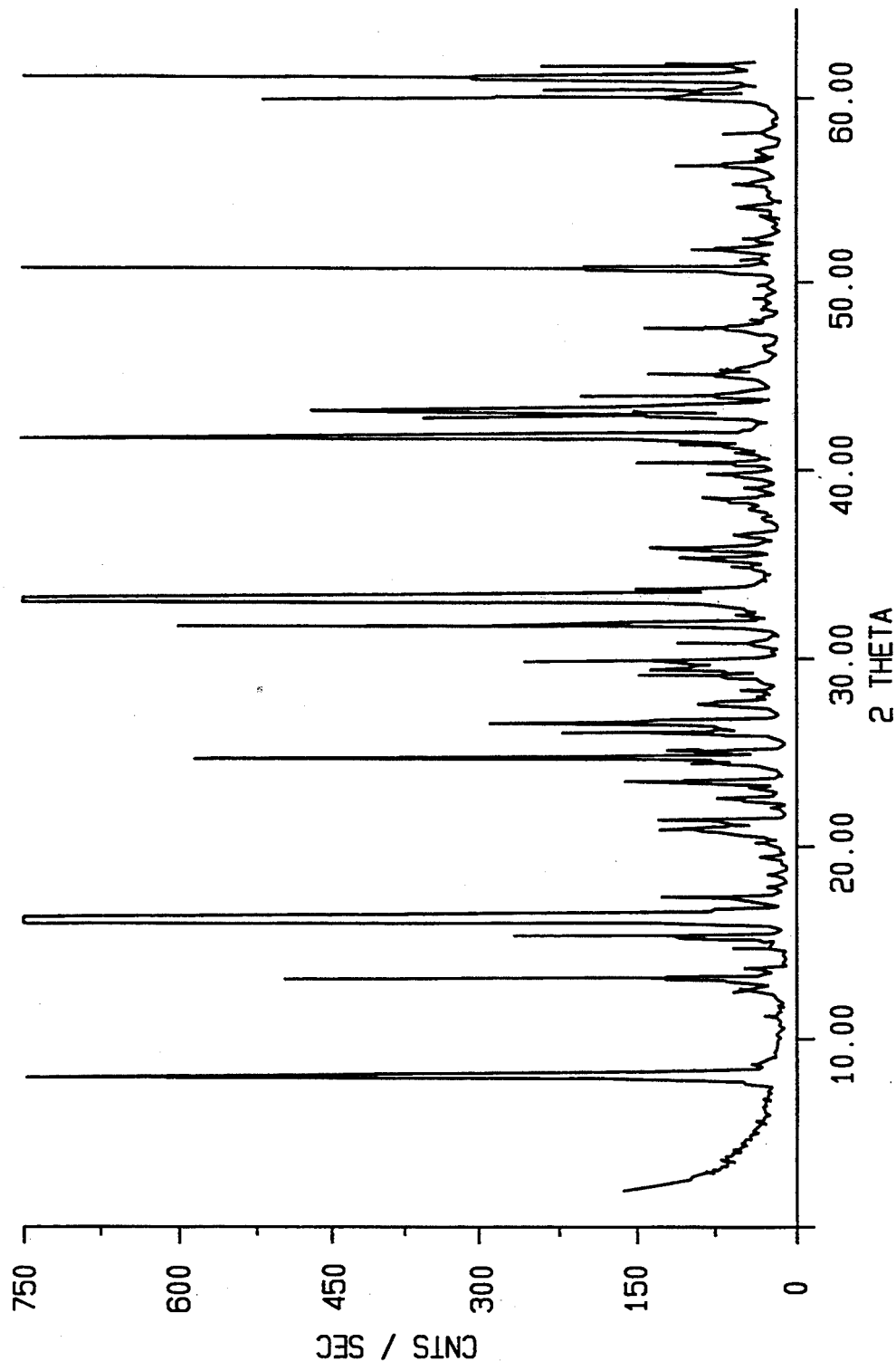

It is certified that error appears in the above-identified patent and that said Letters Patent is hereby corrected as shown below:

Fig. 8, should read

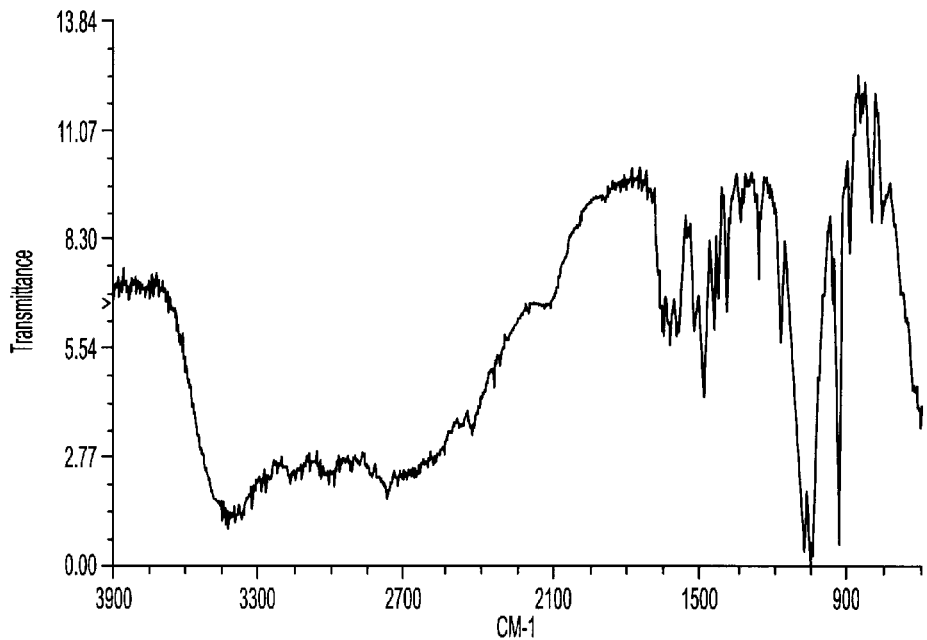

Fig. 8

UNITED STATES PATENT AND TRADEMARK OFFICE
CERTIFICATE OF CORRECTION

PATENT NO. : 5,424,471
APPLICATION NO. : 08/099298
DATED : June 13, 1995
INVENTOR(S) : Kennedy et al.

Figure 11:
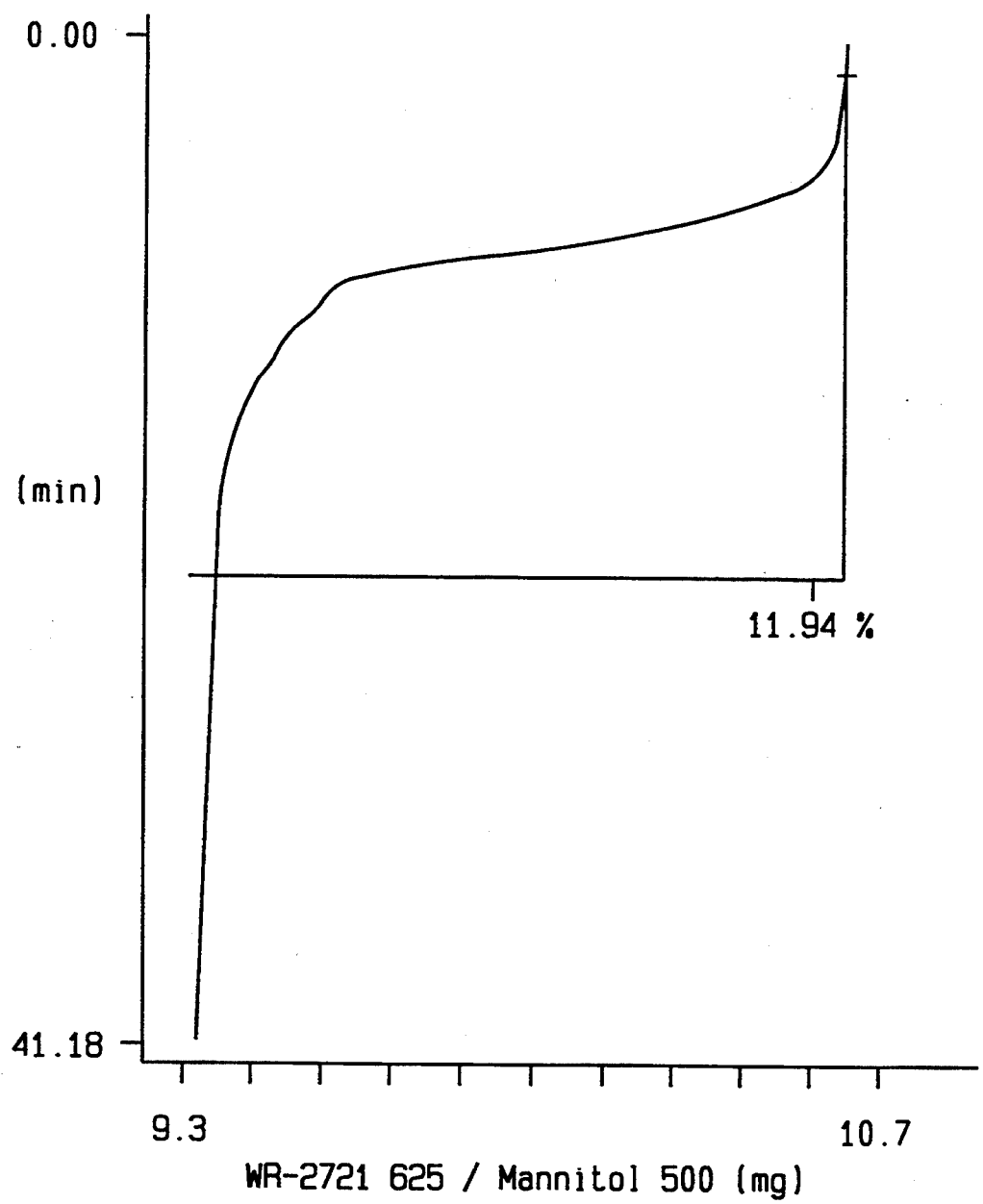

It is certified that error appears in the above-identified patent and that said Letters Patent is hereby corrected as shown below:

Fig. 11, should read

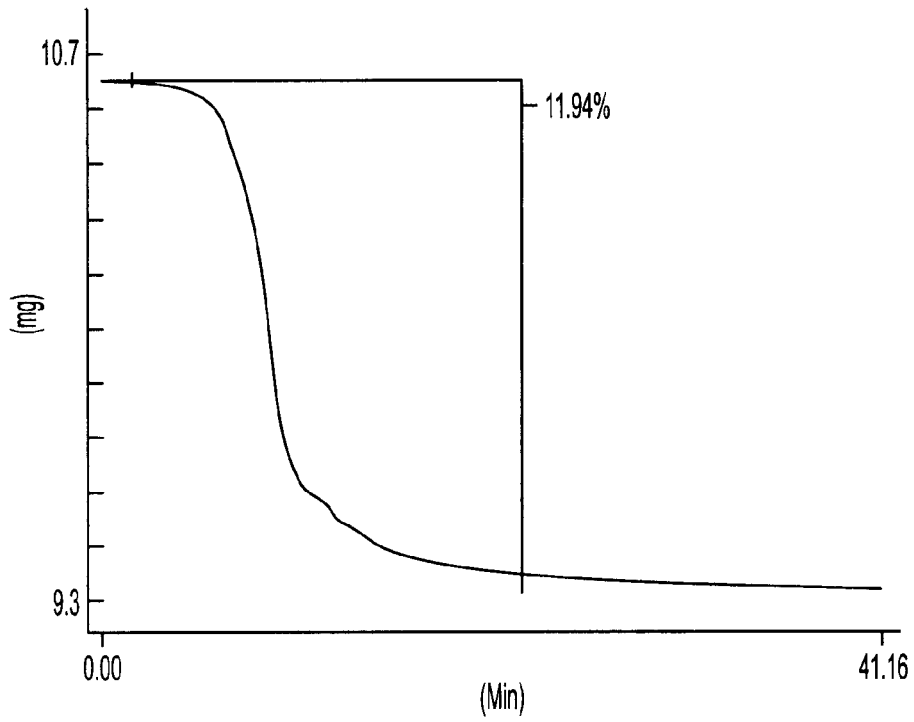

Fig. 11

UNITED STATES PATENT AND TRADEMARK OFFICE
CERTIFICATE OF CORRECTION

PATENT NO.       : 5,424,471
APPLICATION NO.  : 08/099298
DATED            : June 13, 1995
INVENTOR(S)      : Kennedy et al.

Page 8 of 8

Figure 12:
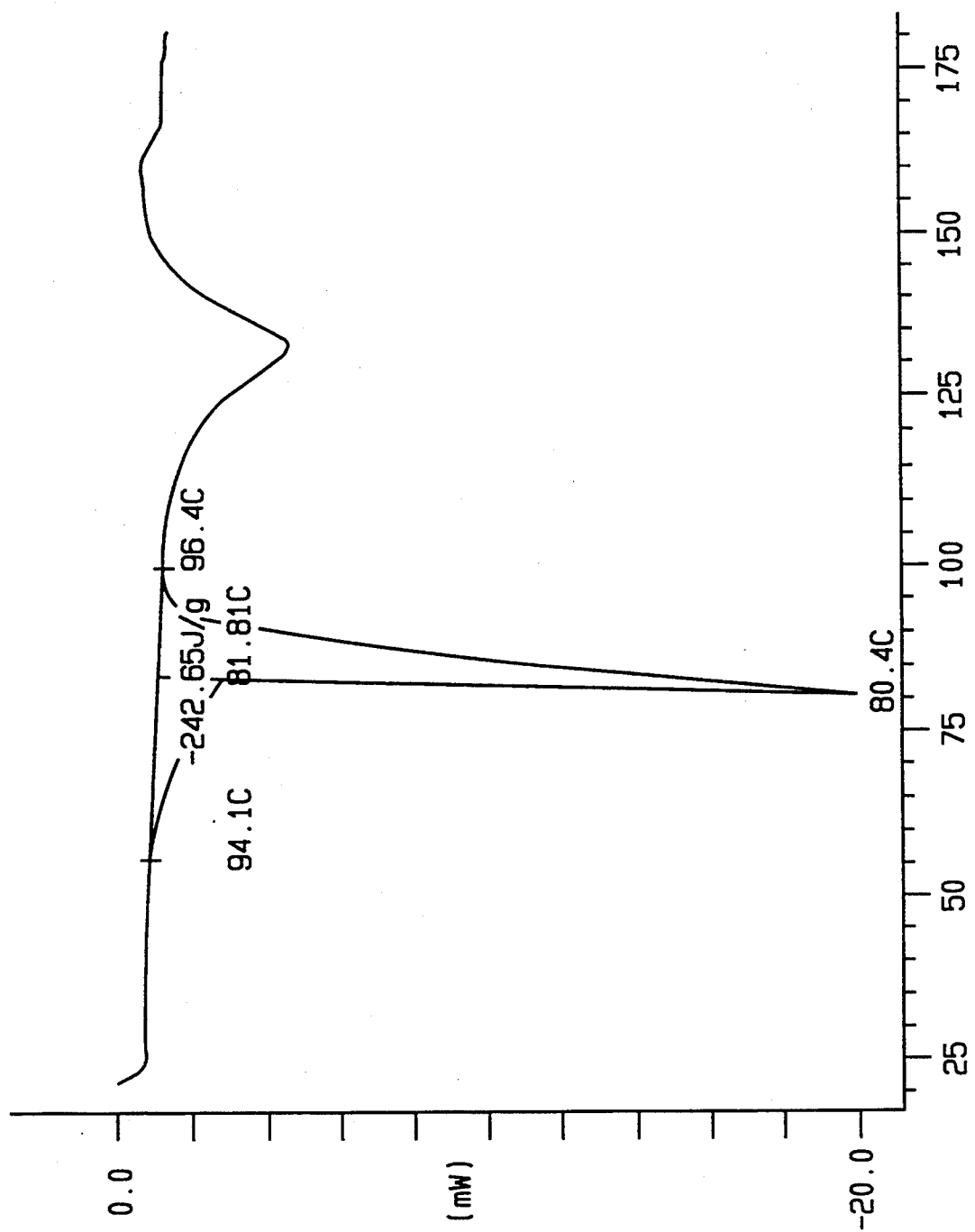

It is certified that error appears in the above-identified patent and that said Letters Patent is hereby corrected as shown below:

Fig. 12, should read

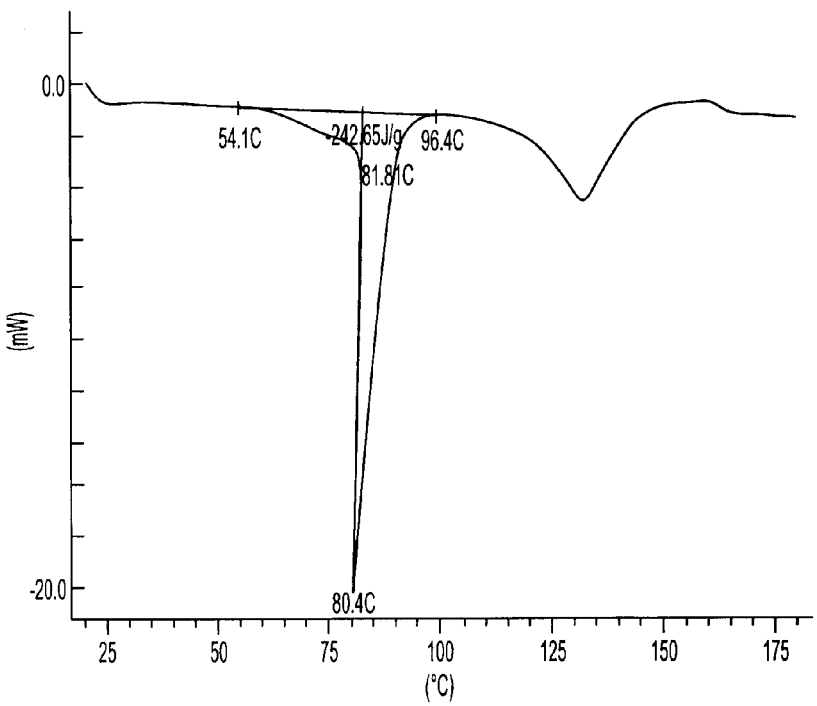

*Fig. 12*

Signed and Sealed this

Twenty-sixth Day of September, 2006

JON W. DUDAS
*Director of the United States Patent and Trademark Office*